US009351486B2

(12) United States Patent
Seifert-Higgins et al.

(10) Patent No.: US 9,351,486 B2
(45) Date of Patent: *May 31, 2016

(54) COMBINATIONS OF DERIVATIZED SACCHARIDE SURFACTANTS AND ETHERAMINE OXIDE SURFACTANTS AS HERBICIDE ADJUVANTS

(71) Applicant: Monsanto Technology LLC, St. Louis, MO (US)

(72) Inventors: Simone Seifert-Higgins, House Springs, MO (US); Christopher I. Bates, Withernwick (GB); William Abraham, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/968,068

(22) Filed: Aug. 15, 2013

(65) Prior Publication Data

US 2014/0113822 A1 Apr. 24, 2014

Related U.S. Application Data

(63) Continuation of application No. 13/002,112, filed as application No. PCT/US2009/049170 on Jun. 30, 2009, now Pat. No. 8,536,095.

(60) Provisional application No. 61/078,113, filed on Jul. 3, 2008.

(51) Int. Cl.
*A01N 57/18* (2006.01)
*A01N 25/30* (2006.01)

(52) U.S. Cl.
CPC ..................................... *A01N 25/30* (2013.01)

(58) Field of Classification Search
None
See application file for complete search history.

(56) References Cited

U.S. PATENT DOCUMENTS

| 3,505,377 A | 4/1970 | Morehouse |
| 3,799,758 A | 3/1974 | Franz |
| 3,853,530 A | 12/1974 | Franz |
| 3,977,860 A | 8/1976 | Franz |
| 4,140,513 A | 2/1979 | Prill |
| 4,315,765 A | 2/1982 | Large |
| 4,405,531 A | 9/1983 | Franz |
| 4,481,026 A | 11/1984 | Prisbylla |
| 4,507,250 A | 3/1985 | Bakel |
| 4,888,325 A | 12/1989 | Schroeder et al. |
| 4,931,080 A | 6/1990 | Chan et al. |
| 5,125,954 A | 6/1992 | Powell et al. |
| 5,164,310 A | 11/1992 | Smith et al. |
| 5,266,553 A | 11/1993 | Champion et al. |
| 5,294,371 A | 3/1994 | Clubley et al. |
| 5,308,827 A | 5/1994 | Sakamoto et al. |
| 5,468,718 A | 11/1995 | Burval et al. |
| 5,504,054 A | 4/1996 | Murphy |
| 5,514,641 A | 5/1996 | Lo et al. |
| 5,543,383 A | 8/1996 | Parker et al. |
| 5,550,115 A | 8/1996 | Garst et al. |
| 5,580,841 A | 12/1996 | Chan et al. |
| 5,658,853 A | 8/1997 | Kassebaum et al. |
| 5,688,902 A | 11/1997 | Bernard et al. |
| 5,693,593 A | 12/1997 | Arnold |
| 5,698,210 A | 12/1997 | Levy |
| 5,750,468 A | 5/1998 | Wright et al. |
| 5,770,543 A | 6/1998 | Garst et al. |
| 5,783,692 A | 7/1998 | Kirby et al. |
| 5,795,847 A | 8/1998 | Nielsen et al. |
| 5,843,866 A | 12/1998 | Parker et al. |
| 5,863,863 A | 1/1999 | Hasebe et al. |
| RE36,149 E | 3/1999 | Gednalske et al. |
| 5,888,934 A | 3/1999 | Townson et al. |
| 5,902,596 A | 5/1999 | Levy |
| 5,906,961 A | 5/1999 | Roberts et al. |
| 5,917,117 A | 6/1999 | Ensley et al. |
| 5,928,563 A | 7/1999 | Klima |
| 5,985,648 A | 11/1999 | Shamoun et al. |
| 6,010,979 A | 1/2000 | Osborn et al. |
| 6,068,849 A | 5/2000 | Mueninghoff et al. |
| 6,107,249 A | 8/2000 | Wikeley |
| 6,117,816 A | 9/2000 | Jimoh et al. |
| 6,117,820 A | 9/2000 | Cutler et al. |
| 6,159,900 A | 12/2000 | Bieringer et al. |
| 6,165,939 A | 12/2000 | Agbaje et al. |
| 6,180,566 B1 | 1/2001 | Nielsen et al. |
| 6,248,695 B1 | 6/2001 | Griffiths et al. |
| 6,255,253 B1 | 7/2001 | Foerster et al. |
| 6,337,078 B1 | 1/2002 | Levy |
| 6,346,262 B1 | 2/2002 | Levy |
| 6,362,393 B1 | 3/2002 | Konzak et al. |
| 6,380,135 B1 | 4/2002 | Reuter et al. |
| 6,383,984 B1 | 5/2002 | Aven |
| 6,395,693 B1 | 5/2002 | Wang |
| 6,432,878 B1 | 8/2002 | Brigance |
| 6,451,735 B1 | 9/2002 | Ottaway et al. |

(Continued)

FOREIGN PATENT DOCUMENTS

| CN | 101406179 A | 4/2009 |
| EP | 0029222 A2 | 5/1981 |
| EP | 0473890 A1 | 3/1992 |
| EP | 0577914 A1 | 1/1994 |
| EP | 0364202 B1 | 8/1995 |
| EP | 0498145 B1 | 11/1995 |
| EP | 0498785 B1 | 12/1997 |
| EP | 0220902 B1 | 4/1998 |
| EP | 0671967 B1 | 2/1999 |
| EP | 1064844 A1 | 1/2001 |
| EP | 0822972 B1 | 8/2001 |
| EP | 0880315 B1 | 11/2001 |

(Continued)

*Primary Examiner* — Alton Pryor
(74) *Attorney, Agent, or Firm* — Senniger Powers LLP; Joseph A. Schaper

(57) ABSTRACT

Efficacious herbicidal compositions comprising a derivatized saccharide surfactant and an amine oxide surfactant are described. The compositions are characterized as having low toxicity and are readily biodegradable.

37 Claims, No Drawings

(56) References Cited

U.S. PATENT DOCUMENTS

| | | | |
|---|---|---|---|
| RE37,866 E | 10/2002 | Wright et al. | |
| RE37,890 E | 10/2002 | Levy | |
| 6,475,954 B2 | 11/2002 | Hamroll et al. | |
| 6,500,782 B1 | 12/2002 | Kassebaum | |
| 6,541,424 B2 | 4/2003 | Roberts et al. | |
| 6,593,299 B1 | 7/2003 | Bennett et al. | |
| 6,617,301 B1 | 9/2003 | Fornara et al. | |
| 6,645,913 B2 | 11/2003 | Brigance | |
| 6,669,949 B2 | 12/2003 | Kennedy et al. | |
| 6,670,306 B2 | 12/2003 | Milius et al. | |
| 6,706,670 B2 | 3/2004 | Kalota et al. | |
| 6,734,141 B2 | 5/2004 | Humble et al. | |
| 6,746,988 B2 | 6/2004 | Hopkinson et al. | |
| 6,747,164 B2 | 6/2004 | Gustavsson et al. | |
| 6,750,178 B1 | 6/2004 | Ramsey et al. | |
| 6,762,289 B1 | 7/2004 | O'Lenick et al. | |
| 6,764,854 B2 | 7/2004 | Konzak et al. | |
| 6,774,087 B1 | 8/2004 | Nakayama et al. | |
| 6,797,673 B1 | 9/2004 | Worthley et al. | |
| 6,797,692 B1 | 9/2004 | Ikonomidou | |
| 6,818,201 B2 | 11/2004 | Cheesman et al. | |
| 6,831,038 B2 | 12/2004 | Volgas et al. | |
| 6,849,577 B1 | 2/2005 | Bean et al. | |
| 6,849,578 B1 | 2/2005 | Wellmann et al. | |
| 6,855,327 B1 | 2/2005 | Lundstedt | |
| 6,992,045 B2 * | 1/2006 | Xu et al. | 504/206 |
| 7,141,532 B2 * | 11/2006 | Graham et al. | 504/206 |
| 7,316,990 B2 | 1/2008 | Tank et al. | |
| 7,723,265 B2 * | 5/2010 | Xu et al. | 504/127 |
| 7,883,715 B2 * | 2/2011 | Abraham et al. | 424/405 |
| 8,536,095 B2 * | 9/2013 | Seifert-Higgins et al. | 504/127 |
| 2001/0019996 A1 | 9/2001 | Soula et al. | |
| 2001/0034304 A1 | 10/2001 | Volgas et al. | |
| 2001/0039321 A1 | 11/2001 | Kennedy et al. | |
| 2001/0051591 A1 | 12/2001 | Ferrett et al. | |
| 2002/0042345 A1 | 4/2002 | Kocur et al. | |
| 2002/0114821 A1 | 8/2002 | Lescota et al. | |
| 2002/0160917 A1 | 10/2002 | Ottaway et al. | |
| 2002/0165115 A1 | 11/2002 | Daniels et al. | |
| 2003/0050194 A1 | 3/2003 | Hopkinson et al. | |
| 2003/0176285 A1 | 9/2003 | Milius et al. | |
| 2003/0176547 A1 | 9/2003 | Diener et al. | |
| 2003/0191026 A1 | 10/2003 | Killick et al. | |
| 2003/0207764 A1 | 11/2003 | Ottaway et al. | |
| 2004/0014603 A1 | 1/2004 | Wollenweber et al. | |
| 2004/0014964 A1 | 1/2004 | Cheesman et al. | |
| 2004/0058821 A1 | 3/2004 | Brigance et al. | |
| 2004/0063586 A1 | 4/2004 | Kirby et al. | |
| 2004/0077498 A1 | 4/2004 | Lynch | |
| 2004/0116294 A1 | 6/2004 | Feucht et al. | |
| 2004/0170657 A1 | 9/2004 | Morvan et al. | |
| 2004/0171488 A1 | 9/2004 | Feucht et al. | |
| 2004/0235668 A1 | 11/2004 | Abribat et al. | |
| 2005/0003963 A1 | 1/2005 | Feucht et al. | |
| 2005/0026780 A1 | 2/2005 | Parrish | |
| 2005/0032649 A1 | 2/2005 | Tank et al. | |
| 2005/0054532 A1 | 3/2005 | Kocur et al. | |
| 2005/0054650 A1 | 3/2005 | Ikonomidou | |
| 2005/0064001 A1 | 3/2005 | Wiesman et al. | |
| 2005/0090396 A1 | 4/2005 | Feucht et al. | |
| 2005/0090397 A1 | 4/2005 | Feucht et al. | |
| 2005/0164884 A1 | 7/2005 | Bramati et al. | |
| 2005/0192182 A1 | 9/2005 | Feucht et al. | |
| 2005/0208144 A1 | 9/2005 | Igari et al. | |
| 2005/0256313 A1 | 11/2005 | Norenberg et al. | |
| 2005/0266999 A1 | 12/2005 | Frisch et al. | |
| 2006/0009360 A1 | 1/2006 | Pifer et al. | |
| 2006/0030628 A1 | 2/2006 | Bokotko et al. | |
| 2006/0142161 A1 | 6/2006 | Bean et al. | |
| 2006/0166898 A1 | 7/2006 | Chen | |
| 2006/0194699 A1 | 8/2006 | Moucharafieh et al. | |
| 2006/0205600 A1 | 9/2006 | Otsubo et al. | |
| 2006/0234868 A1 | 10/2006 | Schnabel et al. | |
| 2007/0022494 A1 | 1/2007 | Fincher et al. | |
| 2007/0054805 A1 | 3/2007 | Krause et al. | |
| 2007/0054806 A1 | 3/2007 | Krause et al. | |
| 2007/0054808 A1 | 3/2007 | Brigance et al. | |
| 2007/0082819 A1 | 4/2007 | Perry et al. | |
| 2007/0087937 A1 | 4/2007 | Leatherman et al. | |
| 2007/0090094 A1 | 4/2007 | Thompson et al. | |
| 2007/0093462 A1 | 4/2007 | Rogers et al. | |
| 2007/0129254 A1 | 6/2007 | Lindner | |
| 2007/0135306 A1 | 6/2007 | Perry et al. | |
| 2007/0197387 A1 | 8/2007 | Polge | |
| 2008/0039322 A1 | 2/2008 | Wang et al. | |
| 2008/0312083 A1 | 12/2008 | Gioia | |
| 2009/0298694 A1 | 12/2009 | Pentland et al. | |
| 2010/0173782 A1 | 7/2010 | Bohus et al. | |
| 2010/0279867 A1 | 11/2010 | Yeritsyan et al. | |

FOREIGN PATENT DOCUMENTS

| | | |
|---|---|---|
| EP | 0767609 B1 | 12/2001 |
| EP | 1063883 B1 | 10/2002 |
| EP | 1006792 B1 | 3/2003 |
| EP | 1164845 B1 | 5/2003 |
| EP | 1156716 B1 | 1/2004 |
| EP | 1326493 B1 | 5/2004 |
| EP | 1337151 B1 | 7/2004 |
| EP | 1642502 A1 | 4/2006 |
| EP | 1366662 B1 | 7/2006 |
| EP | 1829448 A2 | 9/2007 |
| EP | 1714554 B1 | 12/2008 |
| ES | 2033569 A1 | 3/1993 |
| JP | 2009051834 A | 3/2009 |
| JP | 2009114075 A | 5/2009 |
| WO | 9427444 A2 | 12/1994 |
| WO | 9608150 A1 | 3/1996 |
| WO | 9954471 A1 | 10/1999 |
| WO | 0053018 A1 | 9/2000 |
| WO | 0102385 A1 | 1/2001 |
| WO | 0129074 A1 | 4/2001 |
| WO | 0170929 A2 | 9/2001 |
| WO | 0183788 A1 | 11/2001 |
| WO | 03022049 A1 | 3/2003 |
| WO | 03044185 A2 | 5/2003 |
| WO | 03094616 A1 | 11/2003 |
| WO | 03094618 A1 | 11/2003 |
| WO | 2004111183 A2 | 12/2004 |
| WO | 2005044791 A2 | 5/2005 |
| WO | 2005055719 A1 | 6/2005 |
| WO | 2005113779 A2 | 12/2005 |
| WO | 2006014348 A2 | 2/2006 |
| WO | 2006133788 A1 | 12/2006 |
| WO | 2009068226 A2 | 6/2009 |
| WO | 2009098711 A1 | 8/2009 |
| WO | 2009118442 A1 | 10/2009 |
| WO | 2010002836 A2 | 1/2010 |
| WO | 2010003889 A1 | 1/2010 |
| WO | 2010049070 A2 | 5/2010 |
| WO | 2010053385 A1 | 5/2010 |
| WO | 2010100039 A2 | 9/2010 |
| WO | 2010102102 A1 | 9/2010 |

* cited by examiner

COMBINATIONS OF DERIVATIZED SACCHARIDE SURFACTANTS AND ETHERAMINE OXIDE SURFACTANTS AS HERBICIDE ADJUVANTS

REFERENCE TO RELATED APPLICATIONS

This application is a continuation of U.S. application Ser. No. 13/002,112, filed Jun. 13, 2011, now U.S. Pat. No. 8,536,095 B2 issued Sep. 17, 2013, which is the U.S. national stage of International Patent Application Serial No. PCT/US2009/049170, filed Jun. 30, 2009, which claims priority to U.S. Provisional Application Ser. No. 61/078,113, filed Jul. 3, 2008, the entire contents of which are incorporated herein by reference.

FIELD OF THE INVENTION

The present invention generally relates to efficacious herbicidal compositions comprising a derivatized saccharide surfactant and an amine oxide surfactant.

BACKGROUND OF THE INVENTION

Glyphosate (N-phosphonomethyl glycine) is well known as a highly effective and commercially important herbicide useful for combating the presence of a wide variety of unwanted vegetation, including agricultural weeds. Glyphosate is conventionally applied as a formulated product dissolved in water to the foliage of annual and perennial grasses and broadleaf plants and the like, is taken up over a period of time into the leaves, and thereafter translocates throughout the plant.

Usually, glyphosate is formulated in commercial compositions in the form of a water-soluble salt. Various salts of glyphosate, methods for preparing salts of glyphosate, formulations of glyphosate or its salts and methods of use of glyphosate or its salts for killing and controlling weeds and other plants are disclosed in U.S. Pat. No. 4,507,250 to Bakel, U.S. Pat. No. 4,481,026 to Prisbylla, U.S. Pat. No. 4,405,531 to Franz, U.S. Pat. No. 4,315,765 to Large, U.S. Pat. No. 4,140,513 to Prill, U.S. Pat. No. 3,977,860 to Franz, U.S. Pat. No. 3,853,530 to Franz, and U.S. Pat. No. 3,799,758 to Franz. The aforementioned patents are incorporated herein in their entirety by reference. Salts in commercial use include the ammonium salt, alkylamine salts, such as the isopropylamine salt, alkali metal salts, such as the sodium salt, and the trimethylsulfonium salt. However, formulations of glyphosate in its acid form are also used. The IPA salt is widely used in commercial glyphosate formulations. Typical glyphosate salt formulations include aqueous concentrates, requiring simple dilution and distribution in water for application by the end-user, and water-soluble or water-dispersible dry formulations, especially granules, requiring dissolution or dispersion in water prior to application.

A major advantage of the IPA salt over many other salts of glyphosate, such as the potassium salt, has been the good compatibility in aqueous solution concentrate formulations of that salt with a wide range of surfactants. As used herein, the term "surfactant" is intended to include a wide range of adjuvants that can be added to herbicidal glyphosate compositions to enhance the herbicidal efficacy thereof, as compared to the activity of the glyphosate salt in the absence of such adjuvant, irrespective of whether such adjuvant meets a more traditional definition of "surfactant."

Potassium glyphosate concentrate compositions exhibit high specific gravity as compared to solutions of other glyphosate salts thereby allowing high unit per volume loading. For example, one liter of a 30% a.e. by weight glyphosate potassium salt solution at 20° C. contains approximately 376 g glyphosate a.e. per liter, whereas one liter of a 30% a.e. by weight glyphosate IPA salt solution at 20° C. contains approximately 347 g glyphosate a.e. per liter. In other words, at equal a.e. weight concentration, the potassium salt solution delivers about 8% more glyphosate a.e. per liter. It is likely however that serious consideration of glyphosate potassium salt as a herbicidal active ingredient has been inhibited by the relative difficulty in formulating this salt as aqueous solution concentrate ("SL") formulations together with preferred surfactant types. For example, a widely used surfactant in glyphosate IPA salt compositions, namely polyoxyethylene (15) tallowamine of formula (3) above, is highly incompatible in aqueous solution with glyphosate potassium salt. PCT Publication No. WO 00/15037 notes the low compatibility of alkoxylated alkylamine surfactants in general with high-strength glyphosate concentrates.

Under most application conditions, the herbicidal efficacy of glyphosate can be significantly enhanced by including one or more surfactants in the composition to be applied. It is believed that such surfactants act partly by facilitating the penetration of glyphosate, a relatively hydrophilic compound, through the rather hydrophobic cuticle which normally covers the external above-ground surfaces of higher plants. The surfactant can be provided in the concentrate formulation, or it can be added by the end user to the diluted spray composition.

Surfactants tending to give the most useful enhancement of glyphosate herbicidal effectiveness are generally but not exclusively cationic surfactants, including surfactants which form cations in aqueous solution or dispersion at pH levels of around 4-5 characteristic of SL formulations of monobasic salts of glyphosate. Examples are long-chain (typically $C_{12}$ to $C_{18}$) ethoxylated tertiary alkylamine surfactants and quaternary alkylammonium surfactants. An especially common tertiary alkylamine surfactant used in aqueous solution concentrate formulations of glyphosate IPA salt is the very hydrophilic surfactant polyoxyethylene (15) tallowamine, i.e., tallowamine having in total about 15 moles of ethylene oxide in two polymerized ethylene oxide chains attached to the amine group.

A drawback of ethoxylated tertiary alkylamine surfactants known in the art is that when included in concentrate formulations at levels consistent with good herbicidal performance, they tend to be categorized as eye and skin irritants, have elevated oral and aquatic toxicity as compared to some other surfactants known in the art, and typically do not have a ready biodegradable classification. In some jurisdictions, aquatic toxicity or other environmental regulatory issues such as caution or warning labeling may dictate how much, if any, surfactant is incorporated in the compositions of the invention. In contrast, glyphosate has been found to have low animal toxicity because the enzyme system on which it acts is specific to plants. In the case of commercial glyphosate formulations, the ethoxylated tertiary alkylamine surfactants used as bioefficacy enhancers are typically more toxic than glyphosate.

A further drawback of ethoxylated tertiary alkylamine surfactants is they tend to form a stiff gel when combined with water which adds to the complexity and expense of manufacturing formulations containing such surfactants, by making it difficult to clean vessels and process piping. In practice, this problem is ameliorated by adding an anti-gelling agent, such as polyethylene glycol, to the surfactant.

A class of alkyletheramine, alkyletherammonium salt and alkyletheramine oxide surfactants has been disclosed in U.S.

Pat. No. 5,750,468 to be suitable for preparation of aqueous solution concentrate formulations of various glyphosate salts, including potassium salt. It is disclosed therein that an advantage of the subject surfactants when used in an aqueous composition with glyphosate salts is that these surfactants permit the glyphosate concentration of the composition to be increased to very high levels. The oxide surfactants are also reported to have reduced eye irritancy.

Nonionic surfactants, such as for example alkylpolyglucosides ("APG"), are generally reported to be less effective in enhancing herbicidal activity than cationic or amphoteric surfactants when used as the sole surfactant component of SL formulations of glyphosate salt. Advantageously however, as compared to ethoxylated tertiary alkylamine surfactants, alkylpolyglucoside surfactants are generally classified as non-toxic and ready biodegradable. In particular, those surfactants are typically classified as having low oral toxicity, as being biodegradable with no potential for bioaccumulation, and as having no ecotoxicity. Those features are especially desirable because it minimizes exposure risks to the user and minimizes environmental impact.

The use of alkyl polyglucoside surfactants in glyphosate formulations creates other problems.

For example, the addition of such alkyl polyglucosides generally results in higher viscosity formulations (as compared to formulations without alkyl polyglucosides). Such an increase in the viscosity of these high-strength formulations is undesirable for various reasons. In addition to being more difficult to conveniently pour from the container or to wash residues therefrom, the deleterious effects resulting from higher viscosity formulations is more dramatically observed with respect to pumping requirements. Increasing volumes of liquid aqueous glyphosate products are being purchased by end-users in large refillable containers sometimes known as shuttles, which typically have an integral pump or connector for an external pump to permit transfer of liquid. Liquid aqueous glyphosate concentrates are also shipped in bulk, and in large tanks having a capacity of up to about 100,000 liters. The liquid is commonly transferred by pumping to a storage tank at a facility operated by a wholesaler, retailer or cooperative, from which it can be further transferred to shuttles or smaller containers for onward distribution. Because large quantities of glyphosate formulations are purchased and transported in early spring, the low temperature pumping characteristics of such formulations are extremely important.

In some commercial applications it is desirable to dye glyphosate formulations blue or green in order to distinguish the glyphosate product from other herbicidal products. However, glyphosate concentrate formulations comprising an alkylpolyglucoside (e.g., Agrimul™ APG-2067 and 2-ethylhexyl glucoside) surfactant, such as described in WO 00/15037, are generally dark brown in color having a color value of 14 to 18 as measured by a Gardner colorimeter. When dye is added to a formulated glyphosate product having a Gardner color greater than about 10, the concentrate remains dark brown in color.

Still further, alkylpolyglucoside surfactants are subject to foaming, especially during dilution, mixing and spraying of the formulation by the user. In many cases the foam is slow to dissipate.

There exists a need for a surfactant system for use as a pesticidal bioefficacy enhancer that is relatively non-toxic, non-irritating and ready biodegradable. Moreover, the surfactant system must be capable of being combined with a pesticide to form a stable pesticidal concentrate having pesticidal efficacy comparable to pesticidal compositions known except containing toxic and/or low biodegradable surfactant systems.

SUMMARY OF THE INVENTION

The present invention provides efficacious herbicidal compositions comprising a derivatized saccharide surfactant and an amine oxide surfactant, the compositions having low toxicity and high biodegradability.

One aspect of the invention is directed to a composition comprising an herbicide, a derivatized saccharide surfactant and an amine oxide surfactant having an oxyalkylene or polyoxyalkylene group bonded to the amine oxide group via a nitrogen-carbon bond. The oxyalkylene or polyoxyalkylene group is capped at a terminus remote from said nitrogen-carbon bond with a hydrocarbyl group via an ether linkage and the weight ratio of the derivatized saccharide surfactant to the amine oxide surfactant is greater than 1:1.

Another aspect of the present invention is directed to a composition comprising an herbicide, a derivatized saccharide surfactant and an amine oxide surfactant having a group corresponding to the formula $R^1—(XR^2)_m—(OR^2)_n—Z—$ attached to the amine oxide group via a carbon-nitrogen bond. $R^1$ is a hydrocarbyl group comprising from about 6 to about 22 carbon atoms, $R^2$ and $R^3$ are independently selected from alkylene groups comprising from 2 to 4 carbon atoms, Z is a carbon-nitrogen bond or an oxyhydrocarbylene group comprising from 2 to 6 carbon atoms, each X is independently an ether, thioether, sulfoxide, ester, thioester or amide linkage, m is an average number from 0 to about 9, n is an average number from 0 to about 5 and $m+n \geq 1$. The weight ratio of the derivatized saccharide surfactant to the amine oxide surfactant is greater than 1:1.

Yet another aspect of the present invention is directed to such a composition having low toxicity wherein the concentrations of the derivatized saccharide and the amine oxide surfactants are such that the low toxicity composition exhibits lesser aquatic toxicity on an $EC_{50}$ basis than a reference composition but provides plant growth control of at least 85 percent of the growth control provided by the reference composition when the composition and reference composition are applied to the plants at the same glyphosate acid equivalent application rate. The reference composition is devoid of the derivatized saccharide but otherwise identical to the low toxicity composition in the nature and concentration of its herbicide, amine oxide surfactant and any other herbicidally active components. The weight ratio of the derivatized saccharide surfactant to the amine oxide surfactant is greater than 1:1. The aquatic toxicity may be measured by any method known in the art, such as by at least one of U.S. Environmental Protection Agency ("EPA") method 2002.0, EPA method 1002, EPA method 2000.0, EPA method 1000, EPA method 2019.0, Organization for Economic Co-Operation and Development ("OECD") Guideline 202 or the method of Annex V of European Union Directive 67/548/EEC.

In another aspect of the present invention, such low toxicity compositions provide growth control equivalent to that provided by the reference composition.

In another aspect of the present invention, a method is provided for preparing the above aqueous herbicidal compositions having decreased aquatic toxicity relative to a reference composition. The method comprises combining the herbicide, water, the derivatized saccharide and the amine oxide surfactant.

Still another aspect of the present invention is directed to such a composition having high biodegradability wherein the concentrations of the derivatized saccharide and the amine oxide surfactants are such that the highly biodegradable composition exhibits greater biodegradability than a reference composition but provides plant growth control of at least 85 percent of the growth control provided by the reference composition when the composition and reference composition are applied to the plants at the same glyphosate acid equivalent application rate. The reference composition is devoid of the derivatized saccharide but otherwise identical to the low toxicity composition in the nature and concentration of its herbicide, amine oxide surfactant and any other herbicidally active components. The weight ratio of the derivatized saccharide surfactant to the amine oxide surfactant is greater than 1:1. The biodegradability may be measured by any method known in the art, such as by at least one of OECD 301, OECD 302B (Zahn-Wellens/EMPA Test), ASTM method D-5864, CEC method L-33-A-934 or EPA method 560/6-82-003.

In another aspect of the present invention, a method is provided for preparing the above aqueous herbicidal compositions of increased biodegradability relative to a reference composition. The method comprises combining the herbicide, water, the derivatized saccharide and the amine oxide surfactant.

Another aspect of the present invention is directed to methods of controlling plant growth comprising applying the compositions of the present invention to the plant.

Other objects and features will be in part apparent and in part pointed out hereinafter.

DESCRIPTION OF THE PREFERRED EMBODIMENTS

In accordance with the present invention, a surfactant system for effective pesticidal bioefficacy enhancement is provided. As compared to surfactant systems known in the art, the surfactant systems of the present invention are efficacious, have low toxicity to aquatic organisms, have "ready biodegradable" classification and can be formulated in high loading in stable solution concentrates having high pesticide concentrations.

In general, low toxicity, biodegradability, effective pesticidal bioefficacy enhancement, high loading and storage stability are achieved by forming a pesticidal composition that is fully loaded with an agriculturally useful amount of a compatible surfactant system predominantly comprising a nonionic derivatized saccharide surfactant, such as an alkylpolysaccharide, and an etheramine oxide surfactant. Although in the following description of the practice of the present invention, particular reference will be made to an alkylpolysaccharide nonionic surfactant, it should be recognized that the principles disclosed herein are generally applicable to other nonionic derivatized saccharide surfactants in combination with an etheramine oxide surfactant. The adaptation of the present invention to other derivatized saccharide surfactants will be readily apparent to those skilled in the art.

It has been discovered that the combination of the alkylpolysaccharide surfactants and etheramine oxide surfactants of the present invention has a substantial enhancing effect on the herbicidal efficacy of glyphosate salt formulations. Moreover, certain combinations of alkylpolysaccharide and etheramine oxides within the preferred ranges described below appear to have an effect greater than the sum of the efficacy enhancing action of those surfactants when applied individually. The weight ratio of the alkylpolysaccharide or other derivatized saccharide surfactant to the etheramine oxide surfactant is preferably greater than 1:1, such as between 1:1 and about 100:1, more preferably between 1:1 and about 10:1, more preferably from about 2:1 to about 10:1, more preferably from about 2:1 to about 8:1, most preferably from about 2:1 to about 6:1.

The surfactant system can be formulated with pesticides including insecticides, fungicides, bactericides, herbicides, acaricides, miticides and plant growth regulators in the form of, for example, concentrate solutions, emulsions, wettable powders, granules, dusts and flowables.

A preferred herbicide is glyphosate, or a salt or ester thereof. Preferred glyphosate salts include mono(isopropylamine) ("IPA"), trimethylsulfonium ("TMS"), monoethanolammonium ("MEA"), monoammonium, diammonium, sodium and potassium, and mixtures thereof. In aqueous glyphosate concentrate compositions of the present invention, the concentration is preferably from about 300 to about 600 grams acid equivalent glyphosate per liter ("g a.e./L"), more preferably from about 400 to about 600 g a.e./L, more preferably from about 450 to about 600 g a.e./L, still more preferably from about 480 to about 600 g a.e./L. The density of the glyphosate formulations of the present invention is typically at least 1.18 grams per milliliter ("g/mL"), such as, for example, 1.21, 1.25. 1.3, 1.35, 1.4 or even 1.45 g/mL. In solid concentrates of the present invention a concentration of from about 20 to about 90 weight percent glyphosate acid equivalent ("wt % a.e.") is preferred, more preferably about 30 to about 80 wt % a.e., most preferably from about 40 to about 80 wt % a.e. Diluted tank mixtures preferably contain a glyphosate concentration of from about 1 to about 20 grams acid equivalent per liter.

In formulations of the present invention, including tank mixes, aqueous solution concentrates and dry formulations, the ratio (by weight) of the glyphosate a.e. to the total surfactant content is preferably in the range of from about 1:1 to about 10:1, more preferably from about 2:1 to about 10:1, most preferably from about 2:1 to about 5:1. The ratio (by weight) of the glyphosate a.e. to the alkylpolysaccharide or other derivatized saccharide surfactant content is preferably in the range of between about 1:1 and about 20:1, more preferably between about 1:1 and about 10:1, more preferably from about 2:1 to about 5:1, most preferably from about 3:1 to about 4.5:1. The ratio (by weight) of the glyphosate a.e. to the etheramine oxide surfactant content is preferably in the range of from about 5:1 to about 25:1, more preferably from about 10:1 to about 20:1, more preferably from about 12:1 to about 16:1.

Among the derivatized saccharide surfactants, preferred classes include alkylpolysaccharides; alkylesters and alkoxylated alkylesters of saccharides; saccharide amines; silicone functionalized saccharide derivatives; and mixtures thereof. In some embodiments, wherein a mixture of derivatized saccharide surfactants are present, the surfactant mixture predominantly comprises one or more alkylpolysaccharides.

In some embodiments, alkylpolysaccharide surfactants suitable for use in herbicidal compositions of the present invention predominantly comprise one or more chemically stable surfactants having formula (1):

$$H[(R^1-(XR^2)_m-)_x-(NR^3)_n-(R^8O)_p-(R^4)_q-(NR^5R^6-(CH_2)_r-)_s-(NR^7)_t(\text{sug})_u OH]_v[A]_w \quad (1)$$

In reference to formula (1), $R^1$ a straight or branched chain substituted or unsubstituted hydrocarbylene selected from alkyl, alkenyl, alkylphenyl, alkenylphenyl. Each X is independently an ether, thioether, sulfoxide, ester, thioester or amide linkage, each $R^2$ is independently $C_{2-6}$ hydrocarbylene, m is an average number of 0 to about 8, and x is an average number of 0 to about 6. The total number of carbon atoms in $R^1-(XR^2)_m$ is about 8 to about 24. $R^8$ is independently $C_2$-$C_4$ alkylene and p is an average number of 0 to about 12. $R^3$ is hydrogen or $C_{1-4}$ hydrocarbyl and n is 0 or 1. $R^4$ is $C_{1-4}$ hydrocarbyl or hydrocarbylene and q is 0 or 1. $R^5$ and $R^6$ are independently hydrogen or $C_{1-4}$ hydrocarbyl, r is 0 to 4 and s is 0 or 1. $R^7$ is hydrogen or $C_{1-4}$ hydrocarbyl and t is 0 or 1. A is an anionic entity, and v is an integer from 1 to 3 and w is 0 or 1 such that electrical neutrality is maintained.

In further reference to formula (1), the sug moiety is a saccharide residue, and may be an open or cyclic (i.e., pyranose) structure. The saccharide may be a monosaccharide having 5 or 6 carbon atoms, a disaccharide, an oligosaccharide or a polysaccharide. Examples of suitable saccharide moieties, including their corresponding pyranose form, include ribose, xylose, arabinose, glucose, galactose, mannose, telose, gulose, allose, altrose, idose, lyxose, ribulose, sorbose (sorbitan), fructose, and mixtures thereof. Examples of suitable disaccharides include maltose, lactose and sucrose. Disaccharides, oligosaccharides and polysaccharides can be a combination of two or more identical saccharides, for example maltose (two glucoses) or two or more different saccharides, for example sucrose (a combination of glucose and fructose). The degree of polymerization, u, is an average number from 1 to about 10, from 1 to about 8, from 1 to about 5, from 1 to about 3, and from 1 to about 2.

In still further reference to formula (1), when $R^1$ is a hydrophobic group and m, n, p, q, s and t are 0, $R^1$ is generally attached at the sug 1-position, but can be attached at the 2-, 3-, or 4-positions rather than the 1-position (thereby giving, e.g. a glucosyl or galactosyl as opposed to a glucoside or galactoside). For disaccharides and oligosaccharides, the additional saccharide units are generally attached to the previous saccharide unit's 2-position, but attachment through the 3-, 4- and 6-positions can occur.

Optionally, the derivatized saccharide surfactant is an alkyl polysaccharide surfactant having formula (2):

$$R^{11}\text{—O—}(sug)_u \tag{2}$$

wherein $R^{11}$ is a straight or branched chain substituted or unsubstituted hydrocarbyl selected from alkyl, alkenyl, alkylphenyl, alkenylphenyl having from about 4 to about 22 carbon atoms, wherein sug and u are as defined above. As known to those skilled in the art, as depicted in formula (2), $R^{11}$ is linked to a sug oxygen. In various particular embodiments, the polysaccharide surfactant may be an alkyl polyglucoside of formula (2) wherein: $R^{11}$ is a branched or straight chain alkyl group preferably having from 4 to 22 carbon atoms, more preferably from 8 to 18 carbon atoms, or a mixture of alkyl groups having an average value within the given range; sug is a glucose residue (e.g., a glucoside); and u is between 1 and about 5, and more preferably between 1 and about 3.

Examples of surfactants of formula (2) are known in the art. Representative surfactants are presented in Table 1 below wherein for each surfactant sug is a glucose residue.

TABLE 1

| Trade name | $R^{11}$ | u |
|---|---|---|
| APG 225 | $C_{8-12}$ alkyl | 1.7 |
| APG 325 | $C_{9-11}$ alkyl | 1.5 |
| APG 425 | $C_{8-16}$ alkyl | 1.6 |
| APG 625 | $C_{12-16}$ alkyl | 1.6 |
| GLUCOPON 600 | $C_{12-16}$ alkyl | 1.4 |
| PLANTAREN 600 | $C_{12-14}$ alkyl | 1.3 |
| PLANTAREN 1200 | $C_{12-16}$ alkyl | 1.4 |
| PLANTAREN 1300 | $C_{12-16}$ alkyl | 1.6 |
| PLANTAREN 2000 | $C_{8-16}$ alkyl | 1.4 |
| Agrimul PG 2076 | $C_{8-10}$ alkyl | 1.5 |
| Agrimul PG 2067 | $C_{8-10}$ alkyl | 1.7 |

TABLE 1-continued

| Trade name | $R^{11}$ | u |
|---|---|---|
| Agrimul PG 2072 | $C_{8-16}$ alkyl | 1.6 |
| Agrimul PG 2069 | $C_{9-11}$ alkyl | 1.6 |
| Agrimul PG 2062 | $C_{12-16}$ alkyl | 1.4 |
| Agrimul PG 2065 | $C_{12-16}$ alkyl | 1.6 |
| BEROL AG6202 | 2-ethyl-1-hexyl | |

In some embodiments, the derivatized saccharides are fatty acid esters of a saccharide, disaccharide, oligosaccharide or polysaccharide as depicted in formulae (3A) or (3B):

$$(sug)_u\text{-}(OC(O)R^{21})_x \tag{3A}$$

$$(sug)_u(C(O)\text{—}OR^{21})_x \tag{3B}$$

wherein: sug is as defined above; $R^{21}$ is a straight or branched chain alkyl or alkenyl group having from about 4 to about 22 carbon atoms; u is 1 to about 10; and x is a multiple of u with the average number being from about 1 to about 5, for example, 1.5. Preferred are sucrose or sorbitan sug units, $R^{21}$ having from about 8 to about 18 carbons, u=1, and x=about 1 to about 5. Examples include sorbitan monolaurate (Emsorb 2515), sorbitan monooleate (Emsorb 2500), sorbitan trioleate (Emsorb 2503), sorbitan sesquioleate (Emsorb 2502).

In other embodiments, the derivatized saccharides are alkoxylated fatty acid esters of a saccharide, disaccharide, oligosaccharide or polysaccharide as depicted in formula (4):

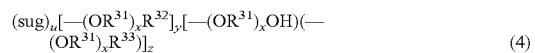

$$(sug)_u[\text{—}(OR^{31})_xR^{32}]_y[\text{—}(OR^{31})_xOH)(\text{—}(OR^{31})_xR^{33})]_z \tag{4}$$

wherein: sug is as defined above; each $R^{31}$ is independently an alkyl having from 2 to about 4 carbon atoms; each $R^{32}$ is independently selected from —OH and —OC(O)$R^{34}$; $R^{33}$ is —OC(O)$R^{34}$; and each $R^{34}$ is independently selected from a straight or branched chain alkyl or alkenyl group having from about 4 to about 22 carbon atoms; u is an average number of from about 1 to about 10, for example 1.5 or 3; each x is independently from about 0 to about 20 and the total x is from 1 to about 60; when u is greater than 1, total x is a multiple of u; y is a multiple of u with the multiplication factor being an average number of from 0 to about 5, for example 1.5; and z is an average number such that z is approximately equal to u. Preferred are: sucrose, glucose or sorbitan sug units; u=about 1; x=about 1 to about 20 and total x from about 1 to about 60; $R^{31}$ having two carbon atoms; $R^{32}$ being —OH or —OC(O)$R^{34}$; and $R^{34}$ being an alkyl or alkenyl moiety having from about 8 to about 18 carbon atoms; y=about 1 to about 4; and z=u. One preferred example is depicted below in formula (5):

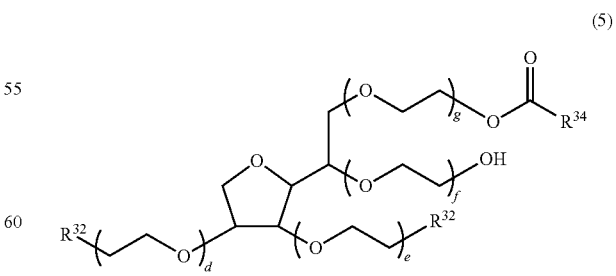

(5)

wherein sug is sorbitan, each $R^{32}$ is —OH, $R^{33}$ is an alkyl or alkenyl having from about 6 to about 20 carbons, and the sum of d, e, f and g is from about 1 to about 50. Examples conforming to formula (5) include polyoxyethylene (20) sorbitan monolaurate (AGNIQUE® SML-20-U; Tween® 20), polyoxyethylene (5) sorbitan monooleate (AGNIQUE® SMO-5), polyoxyethylene (20) sorbitan monooleate (AGNIQUE® SMO-20-U; Tween® 80); and polyoxyethylene (30) sorbitan monooleate (AGNIQUE® SMO-30). Other preferred examples conform to formula (5) wherein sug is sorbitan, each $R^{32}$ is —OC(O)$R^{34}$, $R^{33}$ and $R^{34}$ are each a straight or branched chain alkyl or alkenyl having from about 6 to about 20 carbons, and the sum of d, e, f and g is from about 1 to about 50. Examples include polyoxyethylene (16) sorbitan tristearate (AGNIQUE® STS-16), polyoxyethylene (20) sorbitan tristearate (AGNIQUE® STS-20), polyoxyethylene (20) sorbitan trioleate (Tween® 85; AGNIQUE® STO-2095).

In still other embodiments, the derivatized saccharide surfactant is of formula (6):

$$R^{41}—(NR^{42})_n\text{-}(sug)_u \qquad (6)$$

wherein $R^{41}$ is a straight or branched chain substituted or unsubstituted hydrocarbyl selected from alkyl, alkenyl, alkylphenyl, alkenylphenyl having from about 4 to about 22 carbon atoms, $R^{42}$ is hydrogen or $C_{1-4}$ hydrocarbyl, sug is as defined above, n and u are as defined above. An example of a compound of formula (6) is a glucosamine where $R^{41}$ is $C_8H_{17}$ hydrocarbyl, n and u and are about 1, $R^{42}$ is hydrogen, and sug is an open or cyclic glucose. An example is a cyclic glucosamine derivative of the formula:

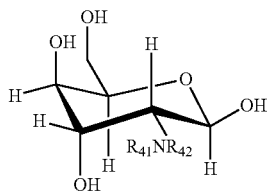

In other variations of the above embodiments, one or more of the hydroxyl groups present in the derivatized saccharide surfactants are substituted with groups that act to improve characteristics such as solubility and efficacy enhancing capabilities.

For example, the compositions of the invention may comprise silicone functionalized alkyl polyglucoside surfactants, as described in U.S. Pat. No. 6,762,289 B1 to O'Lenick et al. (the contents of which are incorporated herein by reference), wherein from 2 to 5 of the hydroxyl groups present on the sug group in an alkyl polysaccharide surfactant is reacted with an organosiloxane to generate a silicone-functionalized alkyl polysaccharide surfactant exhibiting enhanced water solubility. The silicone-functionalize surfactant is represented by chemical formula (7):

$$R^{51}\text{-}(sug)_u(O\text{-organosiloxane})_z \qquad (7)$$

wherein $R^{51}$ represents a straight or branched chain alkyl or alkenyl having from about 8 to about 22 carbon atoms, sug and u are as defined above, and z is an average number of from about 2 to about 5. Each organosiloxane substituent can contain from 1 to about 1000 silicone atoms, said organosiloxane optionally being further substituted with straight or branched chain alkyl, alkenyl or alkoxy groups.

The amine oxide surfactants suitable for use in herbicidal compositions of the present invention are represented by several embodiments. In general, the amine oxide surfactant comprises an oxyalkylene or a polyoxyalkylene group bonded to the amine oxide nitrogen by a nitrogen-carbon bond wherein the outer terminus of the oxyalkylene or polyoxyalkylene chain is capped with a hydrocarbyl group via an ether linkage.

In some embodiments, amine oxide surfactants of the present invention have a group corresponding to the formula $R^1$—$(XR^2)_m$—$(OR^2)_n$—Z— attached to the amine oxide group via a carbon-nitrogen bond, wherein $R^1$ is a hydrocarbyl group comprising from about 6 to about 22 carbon atoms, $R^2$ and $R^3$ are independently selected from alkylene groups comprising from 2 to 4 carbon atoms, Z is a carbon-nitrogen bond or an oxyhydrocarbylene group comprising from about 2 to about 6 carbon atoms, each X is independently an ether, thioether, sulfoxide, ester, thioester or amide linkage, m is an average number from 0 to about 9, n is an average number from 0 to about 5 and m+n≥1.

In various preferred embodiments, the composition comprises an alkyl amine oxide surfactant comprising a hydrophobic moiety and a hydrophilic moiety represented by formula (8):

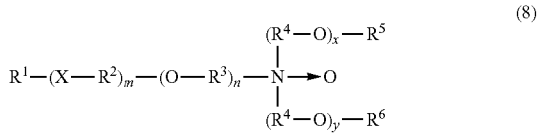

wherein $R^1$ is $C_{1-22}$ a straight or branched chain hydrocarbyl; each X is independently an ether, thioether, sulfoxide, ester, thioester or amide linkage; each $R^2$ is independently $C_{2-6}$ alkylene; each $R^3$ and $R^4$ are independently $C_{2-4}$ alkylene; and $R^5$ and $R^6$ are independently hydrogen, $C_{1-4}$ alkyl or $C_{2-4}$ acyl; x and y are average numbers such that the sum of x and y is from 2 to about 60, more preferably about 2 to about 40, more preferably about 2 to about 20; m is 0 to about 9; and n is 0 to about 5, more preferably about 1 to about 5, still more preferably about 1 to about 3 and when n is not 0 or when m is not 0 and X is and ether, the amine oxide surfactant is termed an etheramine oxide; and m+n is preferably at least one. $R^1$ is preferably a $C_{6-22}$ hydrocarbyl, more preferably a $C_{8-18}$ alkyl, aryl or alkaryl. In some embodiments, m is 0. When m and n are 0, and $R^5$ and $R^6$ are H, $R^1$ is $C_{9-22}$. $R^3$ and $R^4$ are preferably ethyl, n-propyl or i-propyl. In some embodiments, $R^1$ is straight or branched chain $C_{8-18}$ alkyl, aryl or alkaryl, and m is 0. In some other embodiments, $R^1$ is straight or branched chain $C_{8-18}$ alkyl, $R^3$ is ethyl, n-propyl or i-propyl, n is from 1 to about 3, $R^4$ is ethylene, the sum of x and y is from 2 to about 20, and $R^5$ and $R^6$ are hydrogen. In some other embodiments, the surfactant includes commercial surfactants known in the art or referred to herein as "alkyletherdimethylamine oxides" (where n is 1-5, x and y are 0, and $R^5$ and $R^6$ are methyl) and certain "polyoxyalkylene alkyletheramine oxides" (where n is 1-5, x+y is 2 or greater, and $R^5$ and $R^6$ are hydrogen).

A useful class of alkyl amine oxide surfactants are disclosed in U.S. Pat. No. 5,750,468 (the contents of which are incorporated herein) to be suitable for preparation of aqueous solution concentrate formulations of various glyphosate salts, the potassium salt being included in the list of salts mentioned. It is disclosed therein that an advantage of the subject surfactants when used in an aqueous composition with glyphosate salts is that these surfactants permit the glyphosate concentration of the composition to be increased to very high levels. The surfactants of U.S. Pat. No. 5,750,468 predominantly comprise one or more surfactants having formula (9):

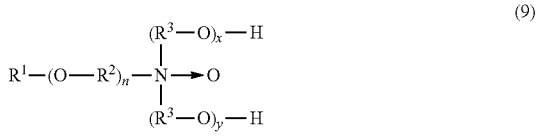

(9)

where $R^1$ is straight or branched chain $C_{6-22}$ alkyl, aryl or alkylaryl group; n is an average number from 0 to about 10, more preferably from about 1 to about 10, and when n is not 0 the amine oxide surfactant is termed an etheramine oxide surfactant; $R^2$ in each of the $(O-R^2)_n$ groups is independently $C_{1-4}$ alkylene; $R^3$ groups are independently $C_{1-4}$ alkylene; and x and y are average numbers such that x+y is in the range from 2 to about 60. When n is 0, $R^1$ is straight or branched chain $C_{9-22}$ alkyl. An example of an amine oxide of formula (9) is the surfactant from Tomah Products designated AO-14-2 wherein $R^1$ is isodecyl, $R^2$ is n-propyl, $R^3$ is ethyl, n is 1, and x+y is 2.

In reference to formula (9), aryl groups, if present in $R^1$, have 5-7, preferably 6, carbon atoms and may or may not be substituted. The alkyl portion in any alkylaryl group comprising $R^1$ has 1-16 carbon atoms. An example of such an alkylaryl group is alkylphenyl, for example nonylphenyl.

In further reference to formula (9), it is preferred that $R^1$ is a straight or branched chain alkyl group having about 8 to about 18 carbon atoms. The $R^2$ substituent closest to the nitrogen atom (the proximal $R^2$ group) is preferred to be a normal propylene, isopropylene or ethylene group. Where the proximal $R^2$ group is n-propylene, n is preferably 1. Where the proximal $R^2$ group is i-propylene or ethylene, n is preferably in the range of from 1 to 5, more preferably from 2 to 3, and all $R^2$ groups are preferably the same. $R^3$ substituents in preferred examples are independently selected from i-propylene and ethylene, with ethylene more preferred. In some embodiments, x+y is preferred to be in the range of from 2 to 20, from 2 to 10, or even from 2 to 5.

In yet another alternative, the amine oxide surfactants predominantly comprise one or more surfactants having formula (10):

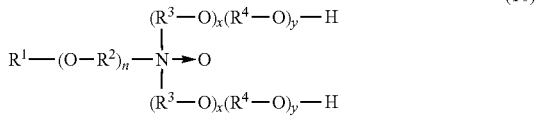

(10)

where $R^1$ is straight or branched chain $C_{6-22}$ alkyl or an aryl or alkylaryl group; n is an average number from 0 to 10, preferably from 1 to about 10 and when n is not 0 the amine oxide surfactant is termed an etheramine oxide surfactant; $R^2$, $R^3$ and $R^4$ are independently $C_{1-4}$ alkylene; and x and y are average numbers such that x+y is in the range from 2 to about 60. When n is 0, $R^1$ is straight or branched chain $C_{9-22}$ alkyl. An example of an amine oxide of formula (12) is the surfactant from Akzo Nobel designated C6602 wherein $R^1$ is $C_{12}$, n is 0, $R^3$ is ethyl, $R^4$ is n-propyl, x=9 and y=2.

In reference to formula (10), aryl groups, if present in $R^1$, have 5-7, preferably 6, carbon atoms and may or may not be substituted with moieties. The alkyl portion is any alkylaryl group comprising $R^1$ has 1-16 carbon atoms. An example of such an alkylaryl group is alkylphenyl, for example nonylphenyl.

In further reference to formula (10), it is preferred that $R^1$ is a straight or branched chain alkyl group having about 8 to about 18 carbon atoms, and is derived from the corresponding alcohol. The $R^2$ substituent closest to the nitrogen atom (the proximal $R^2$ group) is preferred to be a normal propylene, isopropylene or ethylene group. Where the proximal $R^2$ group is n-propylene, n is preferably 1. Where the proximal $R^2$ group is i-propylene or ethylene, n is preferably in the range of from 1 to 5, more preferably from 2 to 3, and all $R^2$ groups are preferably the same. $R^3$ and $R^4$ substituents in preferred examples are independently selected from i-propylene and ethylene, with ethylene more preferred. In some embodiments, x+y is preferred to be in the range of from 2 to 20, from 2 to 10, or even from 2 to 5.

In another embodiment, a class of amine oxide surfactants are represented by formula (11):

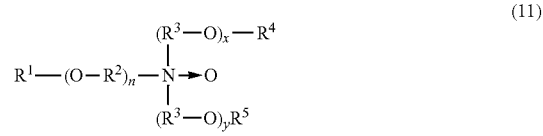

(11)

wherein where $R^1$ is straight or branched chain $C_{6-22}$ alkyl, aryl or alkylaryl group; n is an average number from 0 to about 10 and when n is not 0 the amine oxide is termed an etheramine oxide; $R^2$ and $R^3$ are independently $C_{1-4}$ alkylene; $R^4$ is hydrogen or $C_{1-4}$ alkyl; $R^5$ is $C_{1-4}$ alkyl; and x and y are average numbers such that x+y is in the range from 2 to about 60.

In another embodiment, a class of etheramine oxide surfactants are represented by formula (12):

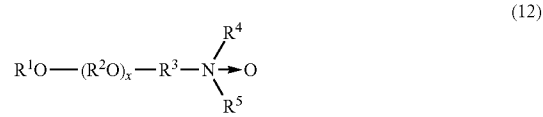

(12)

wherein $R^1$ is a hydrocarbyl or substituted hydrocarbyl having from 1 to about 30 carbon atoms; $R^2$ in each of the $(R^2O)_x$ groups is independently $C_2$-$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, $-(R^6)_n-(R^2O)_yR^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60. In this context, preferred $R^1$, $R^4$, $R^5$ and $R^6$ hydrocarbyl (hydrocarbylene) groups include linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the $(R^2O)_x$ groups is independently $C_2$-$C_4$ alkylene, $R^3$ is a linear or branched alkylene or alkenylene group having from 2 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the $(R^2O)_x$ groups is independently ethylene or propylene, $R^3$ is a linear or branched alkylene or alkenylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the $(R^2O)_x$ groups is independently ethylene or propylene, $R^3$ is an ethylene, propylene or 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the $(R^2O)_x$ groups is independently ethylene or propylene, $R^3$ is an ethylene, propylene, or 2-hydroxypropylene group, $R^4$ and $R^5$ are methyl, and x is an average number from about 4 to about 20.

The herbicidal formulations of the present invention have decreased aquatic toxicity relative to reference compositions comprising alkoxylated tertiary alkylamine surfactants known in the art such as cocoamine having two moles of ethylene oxide ("2 EO") (Ethomeen C/12), cocoamine 5 EO (Ethomeen C/15), cocoamine 10 EO (Ethomeen C/20), cocoamine 15 EO (Ethomeen C/25), tallowamine 2 EO (Ethomeen T/12), tallowamine 2 EO (Ethomeen T/12), tallowamine 5 EO (Ethomeen T/15), tallowamine 10 EO (Ethomeen T/20), and tallowamine 15 EO (Ethomeen T/25). Aquatic toxicity can be measured by any one of various methods known in the art such as, but not limited to, at least one of U.S. Environmental Protection Agency ("EPA") method EPA 2002.0 (*Ceriodaphnia dubia* (water flea) acute); EPA 1002 (*Ceriodaphnia dubia* (water flea) chronic); EPA 2021.0 (*Daphnia magna* (water flea) acute); EPA 2000.0 (*Pimephales promelas* (fathead minnow) acute); EPA 1000 (*Pimephales promelas* (fathead minnow) chronic); EPA 2019.0 (*Oncorhynchus mykiss* (rainbow trout)); Organisation for Economic Co-operation and Development ("OECD") Guideline 202, "*Daphnia* sp., Acute Immobilisation Test and Reproduction Test" (OECD 202 (1984)); and by methods generally specified in Annex V of European Union Directive 67/548/EEC for assessing toxicity to *Daphnia* such as EEC Method C.2 (1992); and by the method described in Powell R. L., Moser E. M., Kimerle R. A., McKenzie D. E., McKee M. 1996, *Use of a miniaturized test system for determining acute toxicity of toxicity identification evaluation fractions*, Ecotoxicol Environ Saf., 1996 Oct, 35(1):1-6). Toxicity is typically reported on a $LC_{50}$ (lethal concentration 50%) basis which refers to the concentration of test substance that is lethal to 50% of the fish within a time period, for example, 24, 48, 72 or 96 hours, or on an $EC_{50}$ (Effective Concentration 50%) basis which is the concentration causing an adverse effect in 50% of the test organisms within a time period, for example, 24, 48, 72 or 96 hours. The formulations of the present invention have an $EC_{50}$ toxicity of less than 90%, 80%, 70%, 60% or even 50% less than the reference compositions as measured by methods known in the art.

The herbicidal formulations of the present invention have increased biodegradability relative to reference compositions comprising alkoxylated tertiary alkylamine surfactants known in the art described above. In general, biodegradability is a measure of the change in the nature of a compound by partial or complete degradation to $CO_2$ and water. Biodegradability can be measured by any one of various methods known in the art such as, but not limited to, at least one of American Society for Testing Materials ("ASTM") method D-5864 Aerobic Aquatic Degradation of Lubricants; Coordinating European Council ("CEC") method L-33-A-934; OECD method 301 (Ready Biodegradability—$CO_2$ in sealed vessels (Headspace Test)); OECD method 302B (Inherent Biodegradability: Zahn-Wellens/EMPA Test); or EPA method 560/6-82-003. In another method, biodegradability can be determined using biological oxygen demand measurement methods known in the art. The biodegradability of some surfactants of the present invention are reported in Table A below.

TABLE A

| Surfactant | Result | Test Method | Interpretation per Method |
|---|---|---|---|
| Tomah PA-14 | 45% in 28 days | OECD 302B | Inherently Biodegradable |
| Tomah E-14-5 | 35% in 28 days | OECD 302B | Inherently Biodegradable |
| Tomah AO-14-2 | 71% in 28 days | OECD 302B | Readily Biodegradable |
| Tomah Q-17-2 | 26% in 28 days | OECD 302B | Inherently Biodegradable |
| $C_{8/10}$ APG | >80-95% after 28 days | OECD 301 | Readily Biodegradable |

Inherently biodegradable is defined as reaching >20% biodegradation in OECD tests over a 28 day period. Readily biodegradable is defined as reaching >60% biodegradation in OECD tests over a 28 day period. Tomah PA-14 is an ether amine surfactant of formula (21) below wherein $R^{41}$ is iso-$C_{10}$, $R^{42}$ is $C_3$, and $R^{43}$ and $R^{44}$ are each hydrogen. Tomah E-14-5 is an ether amine surfactant of formula (21) below wherein $R^{41}$ is iso-$C_{10}$, $R^{42}$ is $C_3$, and $R^{43}$ and $R^{44}$ are each —$(R^{45}O)_x{}^4R^{46}$, wherein $R^{45}$ is $C_2$ alkylene, $R^{46}$ is hydrogen and total $x^4$ is 5. Tomah AO-14-2 is an amine oxide of formula (9) wherein $R^1$ is iso-$C_{10}$, $R^2$ is $C_3$, n is 1, $R^3$ is $C_2$ and x+y is 5. Tomah Q-17-2 is a quaternary amine oxide of formula (16) wherein $R^1$ is iso-$C_{13}$, n is 0, $R^5$ is $C_3$, $R^2$ is —$(CH_2CH_2O)_xH$, $R^3$ is —$(CH_2CH_2O)_yH$, $R^4$ is methyl and x+y is 2. $C_{8/10}$ APG is an alkyl polysaccharide surfactant of formula (2) wherein $R^1$ is $C_{8/10}$.

The herbicidal formulations of the present invention may optionally contain one or more additional surfactants, one or more additional herbicides, and/or other adjuvants or ingredients such as, for example a di-carboxylic acid such as oxalic acid, or a salt or ester thereof. Formulations of the present invention may be prepared on site by the ultimate consumer shortly before application to the foliage of vegetation or weeds to be eliminated or controlled by diluting the aqueous concentrate herbicidal formulations, or by dissolving or dispersing solid particles containing glyphosate. Alternatively, herbicidal formulations of the present invention may be supplied to the ultimate consumer on a "ready to use" basis.

A foam moderating amount of various antifoam agents can be added to the compositions of the present invention to reduce the foaming generated during dilution, mixing and spraying operations. Examples of suitable antifoams include silicone compounds, long-chain alcohols, monocarboxylic fatty acids and salts thereof, high molecular weight fatty esters. Silicone compounds generally contain siloxane units and hydrocarbyl groups, for example, polydimethylsiloxanes having trimethylsilyl end blocking units and dimethylpolysiloxane. Alcohols include octanol (e.g., 2-octanol) and decanol (e.g., 1-decanol). Monocarboxylic fatty acids and their salts typically have hydrocarbyl chains of 10 to 24 carbon atoms. Suitable salts include the alkali metal salts such as sodium, potassium and lithium, and ammonium and alkanolammonium salts. High molecular weight fatty esters include, for example, fatty acid esters of monovalent alcohols, aliphatic $C_{18-40}$ ketones and N-alkylated amino triazines. A weight ratio of antifoam to surfactant from 10:1 to 1:100 is preferred.

Other additives, adjuvants, or ingredients may be introduced into the formulations of the present invention to improve certain properties of the resulting formulations. Although the formulations of the present invention generally show good overall stability and viscosity properties without the addition of any further additives, the addition of a solubilizer (also commonly referred to as a cloud point enhancer or stabilizer) can significantly improve the properties of the formulations of the present invention. In some embodiments, the compounds which enhance the compatibility of such surfactants include amines or quaternary ammonium salts having the formulae:

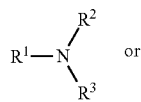
(13)

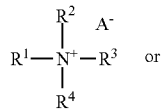
(14)

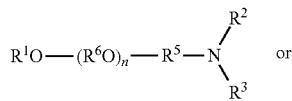
(15)

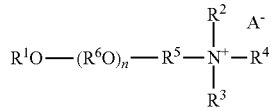
(16)

wherein, for formula (13), $R^1$ is linear or branched alkyl having from 4 to 12 carbon atom or aryl having from about 4 to about 16 carbon atoms, wherein, for formulae (14, (15) and (16) $R^1$ is linear or branched alkyl or aryl having from about 4 to about 16 carbon atoms, and wherein for formulae (13) to (16) $R^2$ is hydrogen, methyl, ethyl, or —(CH$_2$CH$_2$O)$_x$H, $R^3$ is hydrogen, methyl, ethyl, or —(CH$_2$CH$_2$O)$_y$H wherein the sum of x and y is not more than about 5 and the sum of x, y and n is not more than 10; $R^4$ is hydrogen or methyl; $R^6$ in each of the (R$^6$O)$_n$ groups is independently $C_2$-$C_4$ alkylene; $R^5$ is hydrocarbylene or substituted hydrocarbylene having from 2 to about 6 carbon atoms; and A- is an agriculturally acceptable anion. Examples of suitable solubilizers for use with the formulations of the present invention include, for example, cocoamine (Armeen C), dimethylcocoamine (Arquad DMCD), cocoammonium chloride (Arquad C), all of which are manufactured by Akzo Nobel (California), and octylamine.

Additional surfactants and cosurfactants effective in formulating pesticides such as glyphosate, or a salt or ester thereof, with polysaccharide and etheramine oxide surfactants include nonionic, anionic and amphoteric surfactants and cosurfactants as described below and mixtures thereof, wherein the surfactant component is present in an amount sufficient to enhance pesticidal efficacy while maintaining the desired toxicology and biodegradability characteristics. Preferably the sum of the additional surfactants is less than about 10 wt % based on the total weight of the composition.

Cationic surfactants and cosurfactants effective in such glyphosate formulations include:
(a) a secondary or tertiary amine having the formula:

(17)

wherein $R^1$ is hydrocarbyl having from 13 to about 30 carbon atoms, and $R^2$ and $R^3$ are hydrogen or hydrocarbyl having from 1 to about 30 carbon atoms. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^2$ and $R^3$ are independently hydrogen or a linear or branched alkyl or linear or branched alkenyl group having from 1 to about 6 carbon atoms. More preferably, $R^1$ is a linear or branched alkyl or alkenyl group having from about 13 to about 22 carbon atoms, and $R^2$ and $R^3$ are independently hydrogen, methyl or ethyl. In some embodiments of the amine of formula (17), $R^1$ is a linear or branched alkyl group having from about 13 to about 22 carbon atoms, and $R^2$ and $R^3$ are independently linear or branched hydroxyalkyl groups having from 1 to about 6 carbon atoms;
(b) dialkoxylated tertiary amines and quaternary ammonium salt having the formulae:

(18A)

(18B)

wherein $R^{11}$ is hydrocarbyl or substituted hydrocarbyl having from 1 to about 30 carbon atoms, $R^{12}$ in each of the (R$^{12}$O)$_x$ and (R$^{12}$O)$_y$ groups is independently $C_2$-$C_4$ alkylene, $R^{13}$ is hydrogen, or a linear or branched alkyl group having from 1 to about 4 carbon atoms, $R^{14}$ hydrocarbyl or substituted hydrocarbyl having from 1 to about 30 carbon atoms, x and y are independently an average number from 1 to about 40, and X- is an agriculturally acceptable anion. In this context, preferred $R^{11}$ and $R^{14}$ hydrocarbyl groups are linear or branched alkyl, linear or branched alkenyl, linear or branched alkynyl, aryl, or aralkyl groups. Preferably, $R^{11}$ and $R^{14}$ are independently a linear or branched alkyl or linear or branched alkenyl group having from 1 to about 25 carbon atoms, $R^{12}$ in each of the (R$^{12}$O)$_x$ and (R$^{12}$O)$_y$ groups is independently $C_2$-$C_4$ alkylene, $R^{13}$ is hydrogen, methyl or ethyl, and the sum of x and y is an average number from about 2 to about 30. More preferably, $R^{11}$ and $R^{14}$ are independently a linear or branched alkyl group having from 1 to about 22 carbon atoms, $R^{12}$ in each of the (R$^{12}$O)$_x$ and (R$^{12}$O)$_y$ groups is independently ethylene or propylene, $R^{13}$ is hydrogen or methyl, and the sum of x and y is an average number from about 2 to about 20. Even more preferably, $R^{11}$ is a linear or branched alkyl group having from about 8 to about 22 carbon atoms and $R^{14}$ is a linear or branched alkyl group having from 1 to about 22 carbon atoms, $R^{12}$ in each of the (R$^{12}$O)$_x$ and (R$^{12}$O)$_y$ groups is independently ethylene or propylene, $R^{13}$ is hydrogen or methyl, and x is an average number from about 2 to about 20. Most preferably, $R^{11}$ is a linear or branched alkyl group having from about 8 to about 22 carbon atoms and $R^{14}$ is a linear or branched alkyl group having from 1 to about 6 carbon atoms, $R^{12}$ in each of the $(R^{12}O)_x$ and $(R^{12}O)_y$ groups is independently ethylene or propylene, $R^{13}$ is hydrogen or methyl, and x is an average number from about 2 to about 15, or $R^{11}$ and $R^{14}$ are independently a linear or branched alkyl group having from about 8 to about 22 carbon atoms, $R^{12}$ in each of the $(R^{12}O)_x$ and $(R^{12}O)_y$ groups is independently ethylene or propylene, $R^{13}$ is hydrogen or methyl, and x is an average number from about 5 to about 15. Preferred dialkoxylated tertiary amines include Trymeen™ 6617 (from Cognis) and Ethomeen™ C/12, C/15, C/20, C/25, T/12, T/15, T/20 and T/25 (from Akzo Nobel. Preferred dialkoxylated quaternary ammonium surfactants include Ethoquad™ C12 (a PEG 2 coco methyl ammonium chloride from Akzo Nobel), PEG 5 coco methyl ammonium chloride, PEG 5 tallow methyl ammonium chloride, PEG 5 ditallow ammonium bromide, and PEG 10 ditallow ammonium bromide;

(c) monoalkoxylated tertiary and quaternary ammonium salts having the formulae:

(19A)

(19B)

wherein $R^{21}$ and $R^{25}$ are independently hydrogen or hydrocarbyl or substituted hydrocarbyl having from 1 to about 30 carbon atoms, $R^{24}$ is hydrocarbyl or substituted hydrocarbyl having from 1 to about 30 carbon atoms, $R^{22}$ in each of the $(R^{22}O)_x^2$ groups is independently $C_2$-$C_4$ alkylene, $R^{23}$ is hydrogen, or a linear or branched alkyl group having from 1 to about 30 carbon atoms, $x^2$ is an average number from 1 to about 60, and $X^-$ is an agriculturally acceptable anion. In this context, preferred $R^{21}$, $R^{24}$, and $R^{25}$ hydrocarbyl groups are linear or branched alkyl, linear or branched alkenyl, linear or branched alkynyl, aryl, or aralkyl groups. Preferably, $R^{21}$, $R^{24}$ and $R^{25}$ are independently a linear or branched alkyl or linear or branched alkenyl group having from 1 to about 25 carbon atoms, $R^{22}$ in each of the $(R^{22}O)_x^2$ groups is independently $C_2$-$C_4$ alkylene, $R^{23}$ is hydrogen, methyl or ethyl, and $x^2$ is an average number from 1 to about 40. More preferably, $R^{21}$, $R^{24}$ and $R^{25}$ are independently a linear or branched alkyl group having from 1 to about 22 carbon atoms, $R^{22}$ in each of the $(R^{22}O)_x^2$ groups is independently ethylene or propylene, $R^{23}$ is hydrogen or methyl, and $x^2$ is an average number from 1 to about 30. Even more preferably, $R^{211}$ is a linear or branched alkyl group having from about 8 to about 22 carbon atoms, $R^{22}$ in each of the $(R^{22}O)_x^2$ groups is independently ethylene or propylene, $R^{23}$ is hydrogen or methyl, $R^{24}$ and $R^{25}$ are independently a linear or branched alkyl group having from 1 to about 22 carbon atoms, and $x^2$ is an average number from 1 to about 30. Even more preferably, $R^{21}$ is a linear or branched alkyl group having from about 8 to about 22 carbon atoms, $R^{22}$ in each of the $(R^{22}O)_x^2$ groups is independently ethylene or propylene, $R^{23}$ is hydrogen or methyl, $R^{24}$ and $R^{25}$ are independently a linear or branched alkyl group having from 1 to about 6 carbon atoms, and $x^2$ is an average number from about 5 to about 25. Most preferably, $R^{21}$ is a linear or branched alkyl group having from about 16 to about 22 carbon atoms, $R^{22}$ in each of the $(R^{22}O)_x^2$ groups is independently ethylene or propylene, $R^{23}$ is hydrogen or methyl, $R^{24}$ and $R^{25}$ are independently a linear or branched alkyl group having from 1 to about 3 carbon atoms, and $x^2$ is an average number from about 5 to about 25. Preferred monoalkoxylated quaternary ammonium surfactants include PEG 7 $C_{18}$ dimethyl ammonium chloride and PEG 22 $C_{18}$ dimethyl ammonium chloride;

(d) quaternary ammonium salts having the formula:

(20)

wherein $R^{31}$, $R^{33}$ and $R^{34}$ are independently hydrogen or hydrocarbyl or substituted hydrocarbyl having from 1 to about 30 carbon atoms, $R^{32}$ is hydrocarbyl or substituted hydrocarbyl having from 1 to about 30 carbon atoms, and $X^-$ is an agriculturally acceptable anion. In this context, preferred $R^{31}$, $R^{32}$, $R^{33}$, and $R^{34}$ hydrocarbyl groups are linear or branched alkyl, linear or branched alkenyl, linear or branched alkynyl, aryl, or aralkyl groups. Preferably, $R^{31}$ is a linear or branched alkyl or linear or branched alkenyl group having from about 8 to about 30 carbon atoms, and $R^{32}$, $R^{33}$ and $R^{34}$ are independently a linear or branched alkyl or linear or branched alkenyl group having from 1 to about 30 carbon atoms. More preferably, $R^{31}$ is a linear or branched alkyl or linear or branched alkenyl group having from about 8 to about 22 carbon atoms, and $R^{32}$, $R^{33}$ and $R^{34}$ are independently a linear or branched alkyl or linear or branched alkenyl group having from 1 to about 6 carbon atoms. Even more preferably, $R^{31}$ is a linear or branched alkyl group having from about 8 to about 16 carbon atoms, and $R^{32}$, $R^{33}$ and $R^{34}$ are independently a linear or branched alkyl group having from 1 to about 6 carbon atoms. Most preferably, $R^{31}$ is a linear or branched alkyl group having from about 8 to about 14 carbon atoms, and $R^{32}$, $R^{33}$ and $R^{34}$ are methyl. Preferred commercially available quaternary ammonium surfactants include Arquad™ C-50 (a dodecyl trimethyl ammonium chloride from Akzo Nobel) and Arquad™ T-50 (a tallow trimethyl ammonium chloride from Akzo Nobel);

(e) ether amines having the formula:

(21)

wherein $R^{41}$ is hydrocarbyl or substituted hydrocarbyl having from 1 to about 30 carbon atoms; $R^{42}$ is hydrocarbylene or substituted hydrocarbylene having from 2 to about 30 carbon atoms; $R^{43}$ and $R^{44}$ are independently hydrogen, hydrocarbyl or substituted hydrocarbyl having from 1 to about 30 carbon atoms, or —$(R^{45}O)_x^4 R^{46}$, $R^{45}$ in each of the $(R^{45}-O)_x^4$ groups is independently $C_2$-$C_4$ alkylene, $R^{46}$ is hydrogen, or a linear or branched alkyl group having from 1 to about 4 carbon atoms, and $x^4$ is an average number from 1 to about 50. In this context, preferred $R^{41}$, $R^{42}$, $R^{43}$, and $R^{44}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^{41}$ is a linear or branched alkyl, linear or branched alkenyl, linear or branched alkynyl, aryl, or aralkyl group having from 8 to about 25 carbon atoms, $R^{42}$ is a linear or branched alkylene or alkenylene group having from 2 to about 30 carbon atoms, $R^{43}$ and $R^{44}$ are independently hydrogen, a linear or branched alkyl, linear or branched alkenyl, linear or branched alkynyl, aryl, or aralkyl group having from 1 to about 30 carbon atoms, or —$(R^{45}O)_x{}^4 R^{46}$, $R^{45}$ in each of the $(R^{45}O)_x{}^4$ groups is independently $C_2$-$C_4$ alkylene, $R^{46}$ is hydrogen, methyl or ethyl, and $x^4$ is an average number from 1 to about 30. More preferably, $R^{41}$ is a linear or branched alkyl or alkenyl group having from 8 to about 22 carbon atoms, $R^{42}$ is a linear or branched alkylene or alkenylene group having from 2 to about 6 carbon atoms, $R^{43}$ and $R^{44}$ are independently hydrogen, a linear or branched alkyl or alkenyl group having from 1 to about 6 carbon atoms, or —$(R^{45}O)_x{}^4 R^{46}$, $R^{45}$ in each of the $(R^{45}O)_x{}^4$ groups is independently ethylene or propylene, $R^{46}$ is hydrogen or methyl, and $x^4$ is an average number from 1 to about 15. Most preferably, $R^{41}$ is a linear or branched alkyl or alkenyl group having from 8 to about 18 carbon atoms, $R^{42}$ is ethylene or propylene, $R^3$ and $R^4$ are independently hydrogen, methyl, or —$(R^{45}O)_x{}^4 R^{46}$, $R^{45}$ in each of the $(R^{45}O)_x{}^4$ groups is independently ethylene or propylene, $R^{46}$ is hydrogen, and $x^4$ is an average number from 1 to about 5; and (f) aminated alkoxylated alcohols having the following chemical structure:

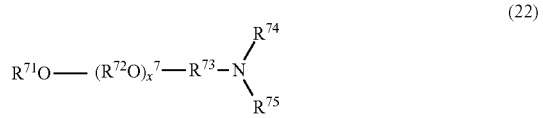

(22)

wherein $R^{71}$ is hydrogen or hydrocarbyl or substituted hydrocarbyl having from 1 to about 30 carbon atoms; $R^{72}$ in each of the $(R^{72}O)_x{}^7$ and $(R^{72}O)_y{}^7$ groups is independently $C_2$-$C_4$ alkylene; $R^{73}$ is hydrocarbylene or substituted hydrocarbylene having from 2 to about 30 carbon atoms; $R^{74}$ and $R^{75}$ are each independently hydrogen, hydrocarbyl or substituted hydrocarbyl having from 1 to about 30 carbon atoms, —$(R^{76})_n{}^7$—$(R^{72}O)_y{}^7 R^{77}$, or $R^{74}$ and $R^{75}$, together with the nitrogen atom to which they are attached, form a cyclic or heterocyclic ring; $R^{76}$ is hydrocarbylene or substituted hydrocarbylene having from 1 to about 30 carbon atoms; $R^{77}$ is hydrogen or a linear or branched alkyl group having 1 to about 4 carbon atoms, $n^7$ is 0 or 1, $x^7$ and $y^7$ are independently an average number from 1 to about 60. In this context, preferred $R^{71}$, $R^{73}$, $R^{74}$, $R^{75}$, and $R^{76}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^{71}$ is a linear or branched alkyl or linear or branched alkenyl group having from about 8 to about 25 carbon atoms, $R^{72}$ in each of the $(R^{72}O)_x{}^7$ groups is independently $C_2$-$C_4$ alkylene, $R^{73}$ is a linear or branched alkylene group having from 2 to about 20 carbon atoms, $R^{74}$ and $R^{75}$ are each independently hydrogen or a linear or branched alkyl group having from 1 to about 6 carbon atoms, and $x^7$ is an average number from 1 to about 30. More preferably, $R^{71}$ is a linear or branched alkyl group having from about 12 to about 22 carbon atoms, $R^{72}$ in each of the $(R^{72}O)_x{}^7$ groups is independently ethylene or propylene, $R^{73}$ is a linear or branched alkylene group having from 2 to about 6 carbon atoms, $R^{74}$ and $R^{75}$ are each independently hydrogen, methyl, or tris (hydroxymethyl)methyl, and $x^7$ is an average number from about 2 to about 30. Even more preferably, $R^{71}$ is a linear or branched alkyl group having from about 12 to about 18 carbon atoms, $R^{72}$ in each of the $(R^{72}O)_x{}^7$ groups is independently ethylene or propylene, $R^{73}$ is ethylene or propylene, $R^{74}$ and $R^{75}$ are each independently hydrogen, methyl or tris(hydroxymethyl)methyl, and $x^7$ is an average number from about 4 to about 20. Most preferably, $R^{71}$ is a linear or branched alkyl group having from about 12 to about 18 carbon atoms, $R^{72}$ in each of the $(R^{72}O)_x{}^7$ groups is independently ethylene or propylene, $R^{73}$ is ethylene, $R^{74}$ and $R^{75}$ are methyl, and $x^7$ is an average number from about 4 to about 20. Preferred monoalkoxylated amines include PEG 13 or 18 $C_{14\text{-}15}$ ether propylamines and PEG 7, 10, 15 or 20 $C_{16\text{-}18}$ ether propylamines (from Tomah) and PEG 13 or 18 $C_{14\text{-}15}$ ether dimethyl propylamines and PEG 10, 15 or 20 or 25 $C_{16\text{-}18}$ ether dimethyl propylamines (from Tomah) and Surfonic™ AGM-550 from Huntsman.

Preferred anionic surfactants effective in forming potassium glyphosate formulations include:

(a) alkyl alkoxylated phosphates having the formula:

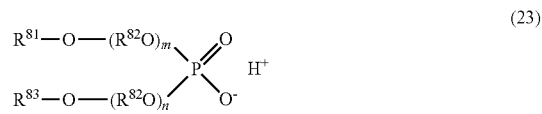

(23)

wherein $R^{81}$ and $R^{83}$ are independently a linear or branched alkyl, linear or branched alkenyl, linear or branched alkynyl, aryl, or aralkyl group having from about 4 to about 30 carbon atoms; $R^{82}$ in each of the m ($R^{82}O$) and the n ($R^{82}O$) groups is independently $C_2$-$C_4$ alkylene; and m and n are independently from 1 to about 30; and (b) alkyl alkoxylated phosphates having the formula:

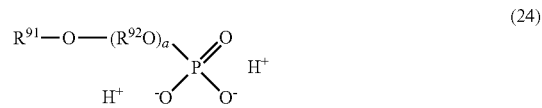

(24)

wherein $R^{91}$ is a linear or branched alkyl, linear or branched alkenyl, linear or branched alkynyl, aryl, or aralkyl group having from about 8 to about 30 carbon atoms; $R^{92}$ in each of the a ($R^{92}O$) groups is independently $C_2$-$C_4$ alkylene; and a is from 1 to about 30. Representative alkyl alkoxylated phosphates include oleth-10 phosphate, oleth-20 phosphate and oleth-25 phosphate.

In addition, nonionic surfactants or cosurfactants effective in such glyphosate formulations include polysiloxane surfactants having the formula:

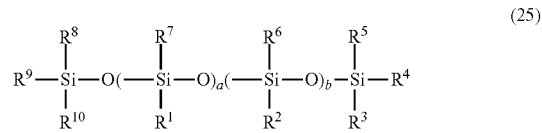

(25)

wherein $R^1$ is —$C_nH_{2n}O(CH_2CH_2O)_m(CH_2CH(CH_3)O)_qX$, n is 0 to 6, a is 0 to about 100, b is 0 to about 10, m is 0 to about 30, q is 0 to about 30, X is hydrogen or a $C_{1-20}$ hydrocarbyl or $C_{2-6}$ acyl group, and $R^2$, $R^3$, $R^4$, $R^5$, $R^6$, $R^7$, $R^8$, $R^9$, $R^{10}$ groups are independently substituted or unsubstituted $C_{1-20}$ hydrocarbyl or nitrogen containing groups. Generally, in preferred embodiments, n is 0 to 6, a is 1 to about 30, b is 0 to about 10, m is 0 to about 30, q is 0 to about 3, X is hydrogen or a $C_{1-6}$ hydrocarbyl or $C_{2-6}$ acyl group, and $R^2$, $R^3$, $R^4$, $R^5$, $R^6$, $R^7$, $R^8$, $R^9$, $R^{10}$ groups are independently substituted or unsubstituted $C_{1-4}$ hydrocarbyl or nitrogen containing groups. In one preferred embodiment, the polysiloxane is a polyoxyethylene heptamethyl trisiloxane wherein $R^1$ is —$C_nH_{2n}O(CH_2CH_2O)_m(CH_2CH(CH_3)O)_qX$, n is 3 or 4, a is 1, b is 0, m is 1 to about 30, q is 0, X is hydrogen or a methyl, ethyl or acetyl group, and $R^2$, $R^3$, $R^4$, $R^5$, $R^6$, $R^7$, $R^8$, $R^9$, $R^{10}$ groups are independently substituted or unsubstituted $C_{1-4}$ hydrocarbyl or nitrogen containing groups. In another preferred embodiment, a is 1 to 5, b is 0 to 10, n is 3 or 4, m is 1 to about 30, q is 0, X is hydrogen or a methyl, ethyl or acetyl group, and $R^2$, $R^3$, $R^4$, $R^5$, $R^6$, $R^7$, $R^8$ain, $R^9$ and $R^{10}$ are methyl groups. In another preferred embodiment, a is 1 to 5, b is 0 to 10, n is 3 or 4, m is 4 to 12, q is 0, X is hydrogen or a methyl or acetyl group, $R^2$, $R^3$, $R^4$, $R^5$, $R^6$, $R^7$, $R^8$, $R^9$ and $R^{10}$ are methyl groups. In a more preferred embodiment, a is 1, b is 0, n is 3 or 4, m is 1 to about 30, b is 0, X is hydrogen or a methyl, ethyl or acetyl group, and $R^2$, $R^8$, $R^3$, $R^4$, $R^5$, $R^6$, $R^7$, $R^8$, $R^9$ and $R^{10}$ are methyl groups. In a further preferred embodiment, a is 1, b is 0, n is 3, m is 8, b is 0, X is methyl and $R^2$, $R^3$, $R^4$, $R^5$, $R^6$, $R^7$, $R^8$, $R^9$ and $R^{10}$ are methyl groups. Trisiloxanes of the above formula are generally described in product literature of Crompton Corporation and in U.S. Pat. No. 3,505,377. Several of such trisiloxanes are ethoxylated organosilicone wetting agents available from Crompton Corporation as Silwet® silicone glycol copolymers. Both liquid organosilicones and dry organosilicones can be used in the surfactant composition; both are included within the scope of the invention. More preferred trisiloxanes are those sold commercially in the United States or elsewhere by Crompton Corporation as Silwet® L-77, Silwet® 408 and Silwet® 800, by Dow-Corning as Sylgard® 309, by Exacto, Inc., as Qwikwet® 100, and by Goldschmidt as Breakthru S-240. In the most preferred polyoxyethylene heptamethyl trisiloxanes, $R^2$ is hydrogen.

Nonionic alkoxylated alcohol surfactants for use in the herbicidal formulations of the present invention have the general structure (26):

$$R_{101}O—(R_{102}O)_xR_{103} \qquad (26)$$

wherein $R_{101}$ is hydrocarbyl or substituted hydrocarbyl having from 1 to about 30 carbon atoms, $R_{102}$ in each of the $(R_{102}O)_x$ groups is independently $C_2$-$C_4$ alkylene, $R_{103}$ is hydrogen, or a linear or branched alkyl group having from 1 to about 4 carbon atoms, and x is an average number from 1 to about 60. In this context, preferred $R_{101}$ hydrocarbyl groups are linear or branched alkyl, linear or branched alkenyl, linear or branched alkynyl, aryl, or aralkyl groups. Preferably, $R_{101}$ is a linear or branched alkyl or linear or branched alkenyl group having from about 8 to about 30 carbon atoms, $R_{102}$ in each of the $(R_{102}O)_x$ groups is independently $C_2$-$C_4$ alkylene, $R_{103}$ is hydrogen, methyl or ethyl, and x is an average number from about 5 to about 50. More preferably, $R_{101}$ is a linear or branched alkyl group having from about 8 to about 25 carbon atoms, $R_{102}$ in each of the $(R_{102}O)_x$ groups is independently ethylene or propylene, $R_{103}$ is hydrogen or methyl, and x is an average number from about 8 to about 40. Even more preferably, $R_{101}$ is a linear or branched alkyl group having from about 12 to about 22 carbon atoms, $R_{102}$ in each of the $(R_{102}O)_x$ groups is independently ethylene or propylene, $R_{103}$ is hydrogen or methyl, and x is an average number from about 8 to about 30. Preferred commercially available alkoxylated alcohols include: Emulgin™ L, Procol™ LA-15 (from Protameen); Brij™ 35, Brij™ 56, Brij™ 76, Brij™ 78, Brij™ 97, Brij™ 98 and Tergitol™ XD (from Sigma Chemical Co.); Neodol™ 25-12 and Neodol™ 45-13 (from Shell); Hetoxol™ CA-10, Hetoxol™ CA-20, Hetoxol™ CS-9, Hetoxol™ CS-15, Hetoxol™ CS-20, Hetoxol™ CS-25, Hetoxol™ CS-30, Plurafac™ A38 and Plurafac™ LF700 (from BASF); ST-8303 (from Cognis); Arosurf™ 66 E10 and Arosurf™ 66 E20 (from Witco/Crompton); ethoxylated (9.4 EO) tallow, propoxylated (4.4 EO) tallow and alkoxylated (5-16 EO and 2-5 PO) tallow (from Witco/Crompton). Also preferred are; SURFONIC™ NP95 of Huntsman (a polyoxyethylene (9.5) nonylphenol); TERGITOL series from Dow and commercially available from Sigma-Aldrich Co. (Saint Louis, Mo.), including TERGITOL-15-S-5, TERGITOL-15-S-9, TERGITOL-15-S-12 and TERGITOL-15-S-15 (made from secondary, linear $C_{11}$ to $C_{15}$ alcohols with an average of 5 moles, 9 moles, 12.3 moles and 15.5 moles of ethoxylation, respectively); the SURFONIC LF-X series from Huntsman Chemical Co. (Salt Lake City, Utah), including L12-7 and L12-8 (made from linear $C_{10}$ to $C_{12}$ alcohols with an average of 7 moles and 8 moles, respectively, of ethoxylation), L24-7, L24-9 and L24-12 (made from linear $C_{12}$ to $C_{14}$ alcohols with an average of 7 moles, 9 moles and 12 moles of ethoxylation, respectively), L68-20 (made from primary, linear $C_{16-18}$ alcohols with an average of 20 moles of ethoxylation) and L26-6.5 (made from linear $C_{12}$ to $C_{16}$ alcohols with an average of 6.5 moles of ethoxylation); and Ethylan 68-30 ($C_{16-18}$ with an average of 20 moles of ethoxylation) available from Akzo Nobel.

In some embodiments of the present invention, the herbicidal efficacy on plants of the low toxicity and/or highly biodegradable compositions of the present invention is from at least 85 percent to 100 percent (i.e., equivalent), for example, 85%, 90%, 95% or 100%, of that provided by a reference composition when the compositions of the present invention and the reference composition are applied to the plants at the same glyphosate acid equivalent application rate and under comparable environmental conditions. The reference composition has the same herbicide content and the same ratio of herbicide to total surfactant as the low toxicity and/or highly biodegradable composition, and comprises the same amine oxide surfactant but is devoid of the alkyl polysaccharide or comprises the same alkyl polysaccharide surfactant but is devoid of the amine oxide surfactant. In some other embodiments of the present invention, the herbicidal efficacy on plants of the low toxicity and/or highly biodegradable compositions of the present invention is greater than that provided by the reference compositions.

The present invention also includes a method for killing or controlling weeds or unwanted vegetation comprising the steps of diluting a liquid concentrate in a convenient amount of water to form a tank mix and applying a herbicidally effective amount of the tank mix to the foliage of the weeds or unwanted vegetation. Similarly included in the invention is the method of killing or controlling weeds or unwanted vegetation comprising the steps of diluting a solid particulate concentrate in a convenient amount of water to form a tank mix and applying a herbicidally effective amount of the tank mix to the foliage of the weeds or unwanted vegetation.

In a herbicidal method of using a composition of the invention, the composition is diluted in a suitable volume of water to provide an application solution which is then applied to foliage of a plant or plants at an application rate sufficient to give a desired herbicidal effect. This application rate is usually expressed as amount of glyphosate per unit area treated, e.g., grams acid equivalent per hectare (g a.e./ha). What constitutes a "desired herbicidal effect" is, typically and illustratively, at least 85% control of a plant species as measured by growth reduction or mortality after a period of time during which the glyphosate exerts its full herbicidal or phytotoxic effects in treated plants. Depending on plant species and growing conditions, that period of time can be as short as a week, but normally a period of at least two weeks is needed for glyphosate to exert its full effect.

Definitions

An "agriculturally useful amount" of a surfactant means containing one or more surfactants of such a type or types and in such an amount that a benefit is realized by the user of the composition in terms of herbicidal effectiveness by comparison with an otherwise similar composition containing no surfactant.

By "fully loaded" is meant having a sufficient concentration of a suitable surfactant to provide, upon conventional dilution in water and application to foliage, herbicidal effectiveness on one or more important weed species without the need for further surfactant to be added to the diluted composition.

By "storage-stable," in the context of an aqueous concentrate composition of glyphosate salt further containing a surfactant, is meant not exhibiting phase separation on exposure to temperatures up to about 50° C. for 14-28 days, and preferably not forming crystals of glyphosate or salt thereof on exposure to a temperature of about 0° C. or even −10° C. for a period of up to about 7 days (i.e., the composition must have a crystallization point of 0° C. or lower). For aqueous solution concentrates, high temperature storage stability is often indicated by a cloud point of about 50° C. or more. Cloud point of a composition is normally determined by heating the composition until the solution becomes cloudy, and then allowing the composition to cool, with agitation, while its temperature is continuously monitored. A temperature reading taken when the solution clears is a measure of cloud point. A cloud point of 50° C. or more is normally considered acceptable for most commercial purposes for a glyphosate SL formulation. Ideally the cloud point should be 60° C. or more, and the composition should withstand temperatures as low as about −10° C. for up to about 7 days without crystal growth, even in the presence of seed crystals of the glyphosate salt.

A surfactant that is described herein as "compatible" with a glyphosate salt at specified surfactant and glyphosate a.e. concentrations is one that provides a storage-stable aqueous concentrate as defined immediately above containing that surfactant and salt at the specified concentrations.

In the context of surfactant content, the expression "predominantly comprises" means that at least about 50%, preferably at least about 75% and more preferably at least about 90%, by weight of the surfactant component is made up of surfactants having the specified features of molecular structure. For the present purpose, the weight or concentration of surfactant component as defined herein does not include essentially non-surfactant compounds that are sometimes introduced with the surfactant component, such as water, isopropanol or other solvents, or glycols (such as ethylene glycol, propylene glycol, polyethylene glycol, etc.).

When an "average number" is recited herein with reference to a structural feature such as oxyethylene units or glucoside units, it will be understood by those skilled in the art that the number of such units in individual molecules in a surfactant preparation typically varies over a range and is not necessarily an integer number. The presence in a composition of individual surfactant molecules having a number of such units outside the stated range in "average number" does not remove the composition from the scope of the present invention, so long as the "average number" is within the stated range and other requirements are met.

The term "hydrocarbyl" as used herein describes organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "substituted hydrocarbyl" as used herein describes hydrocarbyl moieties that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, carboxyl, thiol, acetal, sulfoxide, ester, thioester, ether, thioether, hydroxyalkyl, urea, guanidine, amidine, phosphate, amine oxide, and quaternary ammonium salt.

The term "agriculturally acceptable anion" as used herein refers to any suitable anion that otherwise meets the toxicity and biodegradable limitations of the present invention and does not adversely affect the efficacy of pesticides of the present invention. Examples of agriculturally acceptable anions include chloride, bromide, iodide, sulfate, ethosulfate, phosphate, acetate, propionate, succinate, lactate, citrate, tartrate and glyphosate.

Having described the invention in detail, it will be apparent that modifications and variations are possible without departing from the scope of the invention defined in the appended claims.

EXAMPLES

The following Examples are provided for illustrative purposes only and are not intended to limit the scope of the present invention. The Examples will permit better understanding of the invention and perception of its advantages and certain variations of execution.

| Component Table | | |
|---|---|---|
| GLYPHOSATE | | |
| K-GLY | 47.6 wt % a.e. potassium glyphosate | |
| IPA-GLY | 580 g a.e. per liter IPA glyphosate | |
| SURFACTANT | | |
| A | Emcol CC9 (Witco) | PPO-9 diethylmethylammonium chloride |
| B | Emcol CC25 (Witco) | PPO-25 diethylmethylammonium chloride |
| C | Emcol CC42 (Witco) | PPO-40 diethylmethylammonium chloride |
| D | Emcol CC55 (Witco) | PP0-55 diethylmethylammonium hloride |
| E | Ethylan HB1 (Ackros Chemicals) | 1EO phenol ethoxylate |

Component Table

| | | |
|---|---|---|
| F | Ethylan HB4 | 4EO phenol ethoxylate |
| G | Tomah AO-17-7 (80% a.i.) | Formula (8) with: m = 0; n = 1; $R^1$ = i-tridecyl; $R^3$ = n-propylene; $R^4$ = ethylene; x + y = 7; and $R^5$ and $R^6$ = hydrogen |
| H | Witco C6002 | Formula (10) with: $R^1$ = $C_{12}$; n = 0; $R^3$ = ethylene; $R^4$ = n-propylene; x = 9; and y = 2 |
| I | Witco | dicocoglyceride |
| J | Tomah AO-14-2 | Formula (8) with: m = 0; n = 1; $R^1$ = i-$C_{10}$; $R^3$ = n-propylene; $R^4$ = ethylene; x + y = 2; and $R^5$ and $R^5$ = hydrogen |
| K | Akzo-Nobel AG6210 | Alkylpolyglucoside having a $C_{10}$ hydrophobe |
| L | Akzo-Nobel AG6206 (75% a.i.) | Alkylpolyglucoside having a $C_6$ hydrophobe |
| M | Agrimul PG2062 | Alkylpolyglucoside having a $C_{12-16}$ hydrophobe with 1.4 degree of glycosidation |
| N | Agrimul PG2067 (70% a.i.) | Alkylpolyglucoside having a $C_{8-10}$ hydrophobe with 1.7 degree of glycosidation |
| O | Agrimul PG2069 | Alkylpolyglucoside having a $C_{9-11}$ hydrophobe with 1.6 degree of glycosidation |
| P | Agrimul PG2076 | Alkylpolyglucoside having a $C_{8-10}$ hydrophobe with 1.5 degree of glycosidation |
| Q | Agrimul PG2072 | Alkylpolyglucoside having a $C_{8-16}$ hydrophobe with 1.6 degree of glycosidation |
| R | | Ethoxylated (15EO) tallowamine |
| S | 4:1 blend of Dodigen 4022 (Hoechst) and Tween 20 (Hoechst) | Tween 20 is a polyoxyethylene sorbitan ester. Dodigen 4022 is a quaternary ammonium chloride. |
| T | Genamine CO20 | Cocoamine 2EO |
| U | Atplus 452 (Uniquema) | alkylpolyglucoside |
| V | Burco NPS-225 (Burlington) | alkylpolyglucoside |
| W | Propagen 4317 | |
| X | Propagen HY (40 wt % a.i.) | lauryldimethylhydroxyethylammonium chloride. |
| Y | Synergen PE | poly(5) oxyethylene isotridecyloxypropyl amine |
| Z | Cognis | C8/10 alkylpolyglucoside |
| AA | Huntsman AGM-550 | surfactant of formula (22) where $R^{71}$ is $C_{12-14}$, $R^{72}$ and $R^{73}$ are each isopropyl, $x^7$ is 1, $R^{74}$ is —(CH$_2$CH$_2$O)$_x$H, $R^{75}$ is —(CH$_2$CH$_2$O)$_y$H and x + y is 5 |
| BB | Stepan | |

OTHER

| | | |
|---|---|---|
| antifoam1 | Agnique DF6889 | silicone emulsion |
| antifoam2 | Witco premix #101398 | silicone emulsion |
| antifoam3 | Bevaloid 680 | silicone emulsion |

Comparative Compositions

| Composition | Description |
|---|---|
| 294T6K | 450 g a.e. per liter glyphosate IPA salt in aqueous solution together with a surfactant system as described in U.S. Pat. No. 5,652,197. |
| TDIQ | Touchdown ® IQ: An aqueous concentrate containing 28 wt. % a.e. of the glyphosate diammonium salt, and 8 wt. % alkylpolyglucoside surfactant |
| 139R8H | 30.7 wt % a.e. glyphosate IPA salt in aqueous solution together with 15.4 wt % of ethoxylated (15EO) tallowamine surfactant. |
| 276U4D | 30.7 wt % a.e. glyphosate IPA salt in aqueous solution together with 15.8 wt % of surfactant S (above). |

Formulation Table

| Formul. | Comp1. (wt %) | Comp2. (wt %) | Comp3. (wt %) | Comp4. (wt %) |
|---|---|---|---|---|
| 012R6G | IPA-GLY (34.4%) | T (18.1%) | | |
| 294W6S | IPA-GLY (450 g a.e./L) | Y (90 g/L) | | |
| 299A5V | K-GLY (37%) | N (9.1%) | G (2.9%) | — |
| 299B5T | K-GLY (40%) | N (11.4%) | G (2.5%) | — |
| 299C9O | K-GLY (37%) | N (10.6%) | G (2.3%) | — |
| 351L9P | K-GLY (35.8%) | N (10.2%) | G (2.2%) | antifoam2 (0.01%) |
| 351N8W | K-GLY (36.3) | Z (10.2%) | G (2.2%) | |
| 352K5I | K-GLY (35.8%) | N (9.6%) | G (2.8%) | antifoam2 (0.01%) |
| 362Y7B | IPA-GLY (240 g a.e./L) | Y (239 g/L) | | |
| 413AY6B | K-GLY (35.8%) | U (10.2%) | G (2.2%) | — |
| 413BE3M | K-GLY (35.8%) | U (9.6%) | G (2.8%) | — |
| 439AW2Z | K-GLY (35.8%) | V (10.3%) | G (2.2%) | — |
| 439BT5C | K-GLY (35.8%) | V (9.6%) | G (2.8%) | — |
| 447A7P | K-GLY (37.7%) | Y (7.5%) | antifoam3 (0.5%) | — |
| 447B0I | K-GLY (37.7%) | Y (7.5%) | antifoam3 (0.3%) | — |
| 447C3Z | K-GLY (37.7%) | Y (7.5%) | antifoam3 (0.1%) | — |
| 449AX6G | K-GLY (40%) | N (11.4%) | G (2.5%) | — |
| 449BU7M | K-GLY (39.5%) | N (11.3%) | G (2.5%) | — |
| 449CA3K | K-GLY (39%) | N (11.1%) | G (2.4%) | — |
| 449DT5F | K-GLY (38.5%) | N (11.0%) | G (2.4%) | — |
| 449EH7R | K-GLY (37%) | N (10.6%) | G (2.3%) | — |
| 449FZ1A | K-GLY (36%) | N (10.3%) | G (2.3%) | — |
| 449GO0I | K-GLY (35.5%) | N (10.1%) | G (2.2%) | — |
| 449HJ2P | K-GLY (35%) | N (10.0%) | G (2.2%) | — |
| 449IK9F | K-GLY (37%) | N (9.9%) | G (2.9%) | — |
| 449JL8D | K-GLY (36%) | N (9.6%) | G (2.8%) | — |
| 449KZ6J | K-GLY (35.5%) | N (9.5%) | G (2.8%) | — |
| 449LL5E | K-GLY (35%) | N (9.4%) | G (2.7%) | — |
| 458A6T | K-GLY (35.8%) | N (10.2%) | G (2.2%) | antifoam1 0.1% |
| 458B5N | K-GLY (35.8%) | N (10.2%) | G (2.2%) | antifoam2 0.1% |
| 459A5E | K-GLY (35.8%) | N (9.6%) | G (2.8%) | antifoam1 0.1% |
| 459B2Y | K-GLY (35.8%) | N (9.6%) | G (2.8%) | antifoam2 0.1% |
| 773A2C | K-GLY (40%) | A (10%) | — | — |
| 773B6T | K-GLY (40%) | B (10%) | — | — |
| 774A2X | K-GLY (40%) | C (10%) | — | — |

Formulation Table

| Formul. | Comp1. (wt %) | Comp2. (wt %) | Comp3. (wt %) | Comp4. (wt %) |
|---|---|---|---|---|
| 774B8N | K-GLY (40%) | D (10%) | — | — |
| 774C8K | K-GLY (40%) | E (10%) | — | — |
| 774D4W | K-GLY (40%) | F (10%) | — | — |
| 774E3H | K-GLY (40%) | G (10%) | — | — |
| 774F7B | K-GLY (40%) | H (10%) | — | — |
| 774G1S | K-GLY (40%) | I (10%) | — | — |
| 774H0N | K-GLY (40%) | J (10%) | — | — |
| 779A2C | K-GLY (35%) | K (8.8%) | H (2.9%) | — |
| 779B0J | K-GLY (35%) | K (8.8%) | G (2.9%) | — |
| 779C5V | K-GLY (35%) | L (8.8%) | H (2.9%) | — |
| 779D3G | K-GLY (35%) | L (8.8%) | G (2.9%) | — |
| 779E2R | K-GLY (35%) | N (8.8%) | H (2.9%) | — |
| 779F5K | K-GLY (35%) | N (8.8%) | G (2.9%) | — |
| 779G8J | K-GLY (35%) | O (8.8%) | H (2.9%) | — |
| 779H5H | K-GLY (35%) | O (8.8%) | G (2.9%) | — |
| 779I2M | K-GLY (35%) | P (8.8%) | H (2.9%) | — |
| 779J6Q | K-GLY (35%) | P (8.8%) | G (2.9%) | — |
| 779K7U | K-GLY (35%) | M (8.8%) | H (2.9%) | — |
| 779L7F | K-GLY (35%) | M (8.8%) | G (2.9%) | — |
| 779M0P | K-GLY (35%) | Q (8.8%) | H (2.9%) | — |
| 779N4S | K-GLY (35%) | Q (8.8%) | G (2.9%) | — |
| 785A2D | K-GLY (37%) | L (9.3%) | G (2.9%) | — |
| 785B9K | K-GLY (37%) | L (8.6%) | G (3.5%) | — |
| 785C2A | K-GLY (37%) | L (8.0%) | G (4.1%) | — |
| 785D4Y | K-GLY (37%) | L (7.4%) | G (4.6%) | — |
| 785E8J | K-GLY (40%) | L (10.0%) | G (3.1%) | — |
| 785F1U | K-GLY (40%) | L (9.3%) | G (3.8%) | — |
| 785G7P | K-GLY (40%) | L (8.7%) | G (4.4%) | — |
| 785H6W | K-GLY (40%) | L (8.0%) | G (5.0%) | — |
| 788A1Z | K-GLY (37%) | N (9.9%) | G (2.9%) | — |
| 788B7L | K-GLY (37%) | N (9.3%) | G (3.5%) | — |
| 788C3S | K-GLY (37%) | N (8.6%) | G (4.1%) | — |
| 788D1F | K-GLY (37%) | N (7.9%) | G (4.6%) | — |
| 788E5G | K-GLY (40%) | N (10.7%) | G (3.1%) | — |
| 788F9P | K-GLY (40%) | N (10.0%) | G (3.8%) | — |
| 788G6F | K-GLY (40%) | N (9.3%) | G (4.4%) | — |
| 788H1A | K-GLY (40%) | N (8.6%) | G (5.0%) | — |
| 836Y7G | K-GLY (40%) | N (10.1%) | W (10.7%) | — |
| 838I6T | K-GLY (37%) | X (22.5%) | — | — |
| 847A6D | K-GLY (37%) | L (9.3%) | G (2.9%) | — |
| 847B4K | K-GLY (37%) | L (8.6%) | G (3.5%) | — |
| 847C7L | K-GLY (40%) | L (10.0%) | G (3.1%) | — |
| 850A4S | K-GLY (37%) | N (9.9%) | G (2.9%) | — |
| 901E8J | K-GLY (39.1%; 540 g a.e./L) | N (11.2%) | G (2.4%) | — |
| 901AB7Y | K-GLY (40.0%) | L (8.0%) | G (2.5%) | — |
| 901BT6H | K-GLY (40.0%) | L (6.7%) | G (2.1%) | — |
| 901CW2R | K-GLY (37.0%) | N (10.6%) | G (2.3%) | — |
| 901DV8U | K-GLY (37.0%) | N (11.2%) | G (1.7%) | — |
| 901ER2P | K-GLY (37.0%) | L (3.1%) | N (7.3%) | G (2.9%) |
| 901FT6J | K-GLY (37.0%) | L (5.6%) | N (4.0%) | G (2.9%) |
| 902A3X | K-GLY (36%; 480 g a.e./L) | N (10.2%) | G (2.2%) | — |
| 903T6B | K-GLY (36%; 480 g a.e./L) | N (9.6%) | G (2.8%) | — |
| 903AR2R | K-GLY (40%) | N (8.6%) | G (2.5%) | — |
| 903BQ1P | K-GLY (40%) | N (7.1%) | G (2.1%) | — |
| 919AS3M | K-GLY (37.0%) | L (9.7%) | G (2.5%) | — |
| 919BT8J | K-GLY (40.0%) | L (10.7%) | G (2.5%) | — |
| 919CP0K | K-GLY (37.0%) | N (10.4%) | G (2.5%) | — |
| 919DE7G | K-GLY (40.0%) | N (11.4%) | G (2.5%) | — |
| 922AE5H | K-GLY (40.0%) | L (8.0%) | G (2.5%) | — |
| 922BT1S | K-GLY (40.0%) | L (6.7%) | G (2.1%) | — |
| 922CX4K | K-GLY (37.0%) | N (10.6%) | G (2.3%) | — |
| 922DW1H | K-GLY (37.0%) | N (11.2%) | G (1.7%) | — |
| 922EZ8P | K-GLY (37.0%) | L (3.1%) | G (2.9%) | N (7.3%) |
| 922FR7Q | K-GLY (37.0%) | L (5.6%) | G (2.9%) | N (4.0%) |
| 924AU8N | K-GLY (37.0%) | L (9.7%) | G (2.5%) | — |
| 924BY9M | K-GLY (40.0%) | L (10.7%) | G (2.5%) | — |
| 924CV0L | K-GLY (37.0%) | N (10.3%) | G (2.5%) | — |
| 924DS3B | K-GLY (40.0%) | N (11.4%) | G (2.5%) | — |
| 972AR4D | K-GLY (37.0%) | L (9.3%) | G (2.9%) | — |
| 972BN8J | K-GLY (37.0%) | L (8.6%) | G (3.5%) | — |
| 972CT6L | K-GLY (40.0%) | L (10.0%) | G (3.1%) | — |
| 972DE0C | K-GLY (37.0%) | N (10.6%) | G (2.3%) | — |
| 972ES2A | K-GLY (37.0%) | N (11.2%) | G (1.7%) | — |
| 973AW3C | K-GLY (37.0%) | L (9.7.0%) | G (2.5%) | — |
| 973BY7H | K-GLY (40.0%) | L (10.7%) | G (2.5%) | — |
| 973CR6F | K-GLY (37.0%) | L (10.4%) | G (2.5%) | — |
| 973DQ2V | K-GLY (40.0%) | L (11.4%) | G (2.5%) | — |
| 973EU7K | K-GLY (37.0%) | L (9.9%) | G (2.9%) | — |

In each formulation glyphosate is reported on an acid equivalent basis. Each formulation is made up to 100% with water.

Example 1

Formulations of the 773 and 774 series were prepared by hand mixing, in order, the surfactant, glyphosate and water. The appearance of each formulation was then evaluated with the results reported in Table 1 below:

TABLE 1

| Formulation | Surfactant type | Appearance |
|---|---|---|
| 773A2C | ethoxylated quaternary amine | Hazy before and after water addition |
| 773B6T | ethoxylated quaternary amine | Opaque gel |
| 774A2X | ethoxylated quaternary amine | Severe surfactant gelling |
| 774B8N | ethoxylated quaternary amine | Severe surfactant gelling |
| 774C8K | phenol ethoxylate | Immiscible |
| 774D4W | phenol ethoxylate | Immiscible |
| 774E3H | ethoxylated amine oxide | Opaque before and after water addition |

TABLE 1-continued

| Formulation | Surfactant type | Appearance |
|---|---|---|
| 774F7B | alkoxylated amine oxide | Opaque before and after water addition |
| 774G1S | ethoxylated alkylglyceride | Opaque before and after water addition |
| 774H0N | ethoxylated amine oxide | Opaque before and after water addition |

Example 2

Formulations of the 779 series were prepared by hand mixing, in order, the surfactant, glyphosate and water. Each of those formulations contained an alkylpolyglucoside ("APG") surfactant and an ethoxylated etheramine oxide surfactant ("EAO") in a weight ratio of 3:1. The appearance of each formulation was then evaluated with the results reported in Table 2 below.

TABLE 2

| Formulation | Appearance |
|---|---|
| 779A2C | Opaque both before and after adding water |
| 779B0J | Opaque both before and after adding water |
| 779C5V | Hazy before adding water but transparent after water addition. Low viscosity. |
| 779D3G | Transparent and homogenous before and after water addition. Low viscosity. |
| 779E2R | Hazy before adding water but transparent after water addition. Low viscosity. |
| 779F5K | Transparent and homogenous before and after water addition. Low viscosity. |
| 779G8J | Opaque both before and after adding water |
| 779H5H | Opaque both before and after adding water |
| 779I2M | Hazy before adding water but transparent after water addition. Low viscosity. |
| 779J6Q | Hazy before adding water but transparent after water addition. Low viscosity. |
| 779K7U | Opaque both before and after adding water |
| 779L7F | Opaque both before and after adding water |
| 779M0P | Hazy before adding water but transparent after water addition. Low viscosity. |
| 779N4S | Hazy before adding water but transparent after water addition. Low viscosity. |

Example 3

Formulations of the 785 series were prepared by hand mixing, in order, the surfactants, glyphosate and water. Each of those formulations contained an APG surfactant and an EAO surfactant in varying weight ratios. The glyphosate a.e. to total surfactant weight ratio for each formulation was 4:1. The appearance of each formulation and cloud point was then evaluated with the results reported in Table 3 below:

TABLE 3

| Formulation | APG:EAO | Mixture Appearance | Final Product Appearance | Cloud Point (° C.) |
|---|---|---|---|---|
| 785A2D | 3.2:1 | homogeneous | homogeneous | 76 |
| 785B9K | 2.5:1 | homogeneous | homogeneous | 73 |
| 785C2A | 2.0:1 | hazy | homogeneous | 52 |
| 785D4Y | 1.6:1 | opaque | — | 43 |
| 785E8J | 3.:1 | homogeneous | homogeneous | 61 |

TABLE 3-continued

| Formulation | APG:EAO | Mixture Appearance | Final Product Appearance | Cloud Point (° C.) |
|---|---|---|---|---|
| 785F1U | 2.5:1 | homogeneous | homogeneous | 45 |
| 785G7P | 2.0:1 | homogeneous | homogeneous | 36 |
| 785H6W | 1.6:1 | opaque | opaque | — |

Example 4

Formulations of the 788 series were prepared by hand mixing, in order, the surfactants, glyphosate and water. Each of those formulations contained an APG surfactant and an EAO surfactant in varying weight ratios. The glyphosate a.e. to total surfactant weight ratio for each formulation was 4:1. The appearance of each formulation and cloud point was then evaluated with the results reported in Table 4 below:

TABLE 4

| Formulation | APG:EAO | Mixture Appearance | Final Product Appearance | Cloud Point (° C.) |
|---|---|---|---|---|
| 788A1Z | 3.4:1 | homogeneous | homogeneous | 60 |
| 788B7L | 2.7:1 | homogeneous | homogeneous | 48 |
| 788C3S | 2.1:1 | not homogeneous | homogeneous | 40 |
| 788D1F | 1.7:1 | not homogeneous | homogeneous | 31 |
| 788E5G | 3.4:1 | homogeneous | homogeneous | 42 |
| 788F9P | 2.7:1 | homogeneous | homogeneous | 31 |
| 788G6F | 2.1:1 | not homogeneous | — | — |
| 788H1A | 1.7:1 | not homogeneous | not homogeneous | — |

Example 5

The following formulations were prepared by mixing, in order, glyphosate, water and then the other ingredients. Each of those formulations contained an APG surfactant and an EAO surfactant in varying weight ratios. The cloud point, pH and density of each formulation was then evaluated with the results reported in the table 5a below where APG:EAO refers to the weight ratio of the APG surfactant to the amine oxide surfactant and Gly:Surf refers to the weight ratio of glyphosate acid equivalent to total surfactant content. The stability of each formulation after a period of time (days) was evaluated at varying temperatures with "stab" indicating a stable formulation and PS indicating phase separation. The stability results are reported in Table 5b below.

TABLE 5a

| Formulation | APG:EAO | Gly:Surf | Cloud Point (° C.) | pH | density |
|---|---|---|---|---|---|
| 847A6D | 3.2:1 | 3:1 | 77 | 4.5 | 1.35 |
| 847B4K | 2.5:1 | 3:1 | 65 | 4.4 | 1.35 |
| 847C7L | 3.2:1 | 3:1 | 63 | 4.5 | 1.39 |
| 850A4S | 3.4:1 | 2.9:1 | 57 | 4.4 | 1.36 |
| 901AB7Y | 3.2:1 | 3.8:1 | 63 | 4.4 | 1.38 |
| 901BT6H | 3.2:1 | 4.5:1 | 66 | 4.4 | 1.38 |

TABLE 5a-continued

| Formulation | APG:EAO | Gly:Surf | Cloud Point (° C.) | pH | density |
|---|---|---|---|---|---|
| 901CW2R | 4.6:1 | 2.9:1 | 72 | 4.4 | 1.35 |
| 901DV8U | 6.6:1 | 2.9:1 | 90 | 4.4 | 1.35 |
| 901ER2P | 3.5:1 | 2.8:1 | 80 | 4.4 | 1.35 |
| 901FT8J | 2.1:1 | 3:1 | 83 | 4.5 | 1.35 |
| 903AR2R[a] | 3.4:1 | 3.6:1 | 43 | — | 1.38 |
| 903BQ1P[b] | 3.4:1 | 4.3:1 | 44 | — | 1.38 |
| 919AS3M | 3.9:1 | 3:1 | 87 | 4.5 | 1.35 |
| 919BT8J | 4.3:1 | 3:1 | 75 | 4.4 | 1.39 |
| 919CP0K | 4.2:1 | 2.9:1 | 64 | 4.4 | 1.35 |
| 919DE7G | 4.6:1 | 2.9:1 | 51 | 4.4 | 1.39 |
| 922AE5H[a] | 3.2:1 | 3.8:1 | 63 | — | 1.38 |
| 922BT1S[b] | 3.2:1 | 4.5:1 | 66 | — | 1.38 |
| 922CX4K | 4.6:1 | 2.9:1 | 72 | — | 1.35 |
| 922DW1H | 6.6:1 | 2.9:1 | 91 | — | 1.35 |
| 922EZ8P | 3.6:1 | 2.8:1 | 83 | — | 1.35 |
| 922FR7Q | 3.3:1 | 3:1 | 80 | — | 1.35 |
| 924AU8N | 3.9:1 | 3:1 | 89 | — | 1.35 |
| 924BY9M | 4.3:1 | 3:1 | 68 | — | 1.39 |
| 924CV0L | 4.1:1 | 2.9:1 | 56 | — | 1.37 |
| 972AR4D | 3.2:1 | 3:1 | 80 | — | 1.35 |
| 972BN8J | 2.5:1 | 3:1 | 65 | — | 1.35 |
| 972CT6L | 3.2:1 | 3:1 | 59 | — | 1.39 |
| 972DE0C | 4.6:1 | 2.9:1 | 73 | — | 1.35 |
| 972ES2A | 6.6:1 | 2.9:1 | >95 | — | 1.36 |
| 973AW3C | 3.9:1 | 3:1 | 88 | — | 1.35 |
| 973BY7H | 4.3:1 | 3:1 | 73 | — | 1.39 |
| 973CR6F | 4.2:1 | 2.9:1 | 79 | — | 1.38 |
| 973DQ2V | 4.6:1 | 2.9:1 | 75 | — | 1.39 |
| 973EU7K | 3.4:1 | 2.9:1 | 59 | — | 1.35 |

[a]Weight ratio of glyphosate a.e.:total surfactant = 5:1
[b]Weight ratio of glyphosate a.e.:total surfactant = 6:1

TABLE 5b

| Formulation | Days | 60° C. | 40° C. | 35° C. | RT | 0° C. | −10° C. | −20° C. |
|---|---|---|---|---|---|---|---|---|
| 847A6D | 10 | STAB | — | — | STAB | STAB | STAB | STAB |
| 847B4K | 10 | PS | — | — | STAB | STAB | STAB | STAB |
| 847C7L | 10 | PS | — | — | STAB | STAB | STAB | STAB |
| 850A4S | 7 | PS | — | — | STAB | STAB | STAB | STAB |
| 850A4S | 14 | PS | — | — | STAB | STAB | STAB | STAB |
| 972AR4D | 14 | STAB | STAB | STAB | STAB | STAB | STAB | — |
| 972BN8J | 14 | PS | STAB | STAB | STAB | STAB | STAB | — |
| 972CT6L | 14 | PS | STAB | STAB | STAB | STAB | STAB | — |
| 972DE0C | 14 | STAB | STAB | STAB | STAB | STAB | STAB | — |
| 972ES2A | 14 | STAB | STAB | STAB | STAB | STAB | STAB | — |
| 973AW3C | 14 | STAB | STAB | STAB | STAB | STAB | STAB | — |
| 973BY7H | 14 | STAB | STAB | STAB | STAB | STAB | STAB | — |
| 973CR6F | 14 | STAB | STAB | STAB | STAB | STAB | STAB | — |
| 973DQ2V | 14 | STAB | STAB | STAB | STAB | STAB | STAB | — |
| 973EU7K | 14 | PS | STAB | STAB | STAB | STAB | STAB | — |
| 972AR4D | 21 | STAB | STAB | STAB | STAB | — | STAB | — |
| 972BN8J | 21 | STAB | STAB | STAB | STAB | — | STAB | — |
| 972CT6L | 21 | PS | STAB | STAB | STAB | — | STAB | — |
| 972DE0C | 21 | STAB | STAB | STAB | STAB | — | STAB | — |
| 972ES2A | 21 | STAB | STAB | STAB | STAB | — | STAB | — |
| 973AW3C | 21 | STAB | STAB | STAB | STAB | — | STAB | — |
| 973BY7H | 21 | STAB | STAB | STAB | STAB | — | STAB | — |
| 973CR6F | 21 | STAB | STAB | STAB | STAB | — | STAB | — |
| 973DQ2V | 21 | STAB | STAB | STAB | STAB | — | STAB | — |
| 973EU7K | 21 | PS | STAB | STAB | STAB | — | STAB | — |
| 972AR4D | 28 | STAB | STAB | STAB | STAB | — | STAB | — |
| 972BN8J | 28 | PS | STAB | STAB | STAB | — | STAB | — |
| 972CT6L | 28 | PS | STAB | STAB | STAB | — | STAB | — |
| 972DE0C | 28 | STAB | STAB | STAB | STAB | — | STAB | — |
| 972ES2A | 28 | STAB | STAB | STAB | STAB | — | STAB | — |
| 973AW3C | 28 | STAB | STAB | STAB | STAB | — | STAB | — |
| 973BY7H | 28 | STAB | STAB | STAB | STAB | — | STAB | — |
| 973CR6F | 28 | STAB | STAB | STAB | STAB | — | STAB | — |
| 973DQ2V | 28 | STAB | STAB | STAB | STAB | — | STAB | — |
| 973EU7K | 28 | PS | STAB | STAB | STAB | — | STAB | — |

Example 6

Viscosity Testing

Example VT1

Compositions 901E8J, 902A3X, 903T6B and 294W6S, each containing 0.01% antifoam2, were tested for viscosity over a range of temperatures. Composition 901E8J had viscosity of about 1,000 c.p. at 0° C., about 800 c.p. at 5° C., about 600 c.p. at 10° C. and about 400 c.p. at 20° C. The remaining compositions had viscosities of about 600 c.p. or less at 0° C., about 400 c.p. or less at 5° C., about 250 c.p. or less at 10° C., and about 150 c.p. or less at 20° C.

Bubbling/Foaming Tests

Example B/F1

Compositions 902A3X and 903T6B, comparative composition 294T6K containing 3.0 w/v % antifoam3, and Touchdown® IQ containing 4.0 w/v % antifoam3 were evaluated for bubbling. Air was bubbled through each sample through a flat fan nozzle at pressures of 20 psi, 40 psi and 60 psi with bubbling evaluated at each pressure. The rating scale was as follows: 0=no bubbles; 1=a small number of bubbles throughout the test; 2=a few bubbles; 3=some bubbling; 4=much bubbling; and 5=severe bubbling. The results are reported in the table below:

| Formulation | Comments | 20 psi | 40 psi | 60 psi |
|---|---|---|---|---|
| 294T6K | Lot "A" | 0 | 5 | 4 |
| 294T6K | Lot "B" | 0 | 1 | 1 |
| 294T6K | Lot "B" aged 2 weeks | 0 | 1 | 1 |
| 294T6K | Lot "C" | 0 | 1 | 1 |
| 294T6K | Lot "C" aged 2 weeks | 0 | 1 | 1 |
| 294T6K | Lot "D" aged 2 weeks | 0 | 0/1 | 0/1 |
| 902A3X | — | 0 | 4 | 3 |
| 903T6B | — | 0 | 3/4 | 4 |
| 294T6K | Lot "A" and 2.3 w/w % antifoam1 | 0 | 3 | 0 |
| TDIQ | — | 1 | 3 | 2 |

Antifoam3 continues to be active after aging. Formulations 902A3X and 903T6B did exhibit some bubbling but those compositions did not contain antifoam. Antifoam reduced bubbling.

Example B/F2

A sample of each formulation (30 mL) was added to a 100 mL cylinder and then placed in an oven and heated to 38° C. Each cylinder was removed from the oven and shaken by hand (vertically) for about 10 seconds. The foam height above 30 mL was recorded versus time with the results reported in the table below:

| Formulation | 1 minute | 3 minutes | 12 minutes | 60 minutes |
|---|---|---|---|---|
| 362Y7B | 8.4 cm | 8.2 cm | 8.0 cm | 4.9 cm |
| 139R8H | 3.7 cm | 3.6 cm | 2.8 cm | 0.0 cm |
| 294T6K | 2.7 cm | 3.0 cm | 3.0 cm | 2.7 cm |
| 276U4D | 1.6 cm | 0.7 cm | 0.0 cm | 0.0 cm |
| 902A3X | 2.7 cm | — | 2.8 cm | 1.6 cm |
| 903T6B | 2.2 cm | 2.2 cm | 1.8 cm | 0.5 cm |

The evaluation was repeated to evaluate the effect of antifoam3 and antifoam1 on the formulation foaming capabilities. The results are reported in the table below.

| Formulation | Other | 1 minute | 3 minutes | 12 minutes | 60 minutes |
|---|---|---|---|---|---|
| 139R8H | — | 2.8 cm | 2.6 cm | 2.1 cm | 0.0 cm |
| 276U4D | — | 1.6 cm | 0.6 cm | 0.0 cm | 0.0 cm |
| 362Y7B | — | 8.4 cm | 8.4 cm | 7.6 cm | 3.9 cm |
| 362Y7B | 0.01% Bevaloid antifoam | 2.8 cm | 2.7 cm | 2.5 cm | 1.2 cm |
| 294T6K | — | 1.9 cm | 2.0 cm | 2.1 cm | 1.9 cm |
| 902A3X | 0.01% Agnique DF6889 Antifoam | 2.9 cm | 2.9 cm | 2.8 cm | 1.8 cm |
| 903T6B | 0.01% Agnique DF6889 Antifoam | 2.4 cm | 2.5 cm | 2.4 cm | 1.3 cm |

Efficacy Testing

Spray compositions of the Examples, containing an exogenous chemical, such as glyphosate potassium salt, in addition to the excipient ingredients listed, were evaluated for herbicidal efficacy according to the following method.

The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Concentrate compositions were tested by dilution, dissolution or dispersion in water to form spray compositions. In these spray compositions prepared from concentrates, the concentration of excipient ingredients varied with that of exogenous chemical.

Because the commercially most important herbicidal derivatives of glyphosate are certain salts thereof, the glyphosate compositions useful in the present invention will be described in more detail with respect to such salts. These salts are well known and include ammonium, IPA, alkali metal (such as the mono-, di-, and tripotassium salts), and trimethylsulfonium salts. Salts of glyphosate are commercially significant in part because they are water soluble. The salts listed immediately above are highly water soluble, thereby allowing for highly concentrated solutions that can be diluted at the site of use. In accordance with the method of this invention as it pertains to glyphosate herbicide, an aqueous solution containing a herbicidally effective amount of glyphosate and other components in accordance with the invention is applied to foliage of plants. Such an aqueous solution can be obtained by dilution of a concentrated glyphosate salt solution with water, or dissolution or dispersion in water of a dry (i.e., granular, powder, tablet or briquette) glyphosate formulation.

Exogenous chemicals should be applied to plants at a rate sufficient to give the desired biological effect. These application rates are usually expressed as amount of exogenous chemical per unit area treated, e.g. grams per hectare (g/ha). What constitutes a "desired effect" varies according to the standards and practice of those who investigate, develop, market and use a specific class of exogenous chemicals. For example, in the case of a herbicide, the amount applied per unit area to give 85% control of a plant species as measured by growth reduction or mortality is often used to define a commercially effective rate.

Herbicidal effectiveness is one of the biological affects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The herbicidal effectiveness data set forth herein report "inhibition" as a percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Company in the course of its herbicide business.

The selection of application rates that are biologically effective for a specific exogenous chemical is within the skill of the ordinary agricultural scientist. Those of skill in the art will likewise recognize that individual plant conditions, weather and growing conditions, as well as the specific exogenous chemical and formulation thereof selected, will affect the efficacy achieved in practicing this invention. Useful application rates for exogenous chemicals employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Such compositions can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium, and Zea.

Particularly important species for which glyphosate compositions are used are exemplified without limitation by the following:
  Annual Broadleaves:
  velvetleaf (*Abutilon theophrasti*)
  pigweed (*Amaranthus* spp.)
  buttonweed (*Borreria* spp.)
  oilseed rape, canola, indian mustard, etc. (*Brassica* spp.)
  commelina (*Commelina* spp.)
  filaree (*Erodium* spp.)
  sunflower (*Helianthus* spp.)
  morningglory (*Ipomoea* spp.)
  kochia (*Kochia scoparia*)
  mallow (*Malva* spp.)
  wild buckwheat, smartweed, etc. (*Polygonum* spp.)
  purslane (*Portulaca* spp.)
  russian thistle (*Salsola* spp.)
  sida (*Sida* spp.)
  wild mustard (*Sinapis arvensis*)
  cocklebur (*Xanthium* spp.)
  Annual Narrowleaves:
  wild oat (*Avena fatua*)
  carpetgrass (*Axonopus* spp.)
  downy brome (*Bromus tectorum*)
  crabgrass (*Digitaria* spp.)
  barnyardgrass (*Echinochloa crus-galli*)
  goosegrass (*Eleusine indica*)
  annual ryegrass (*Lolium multiflorum*)
  rice (*Oryza sativa*)
  ottochloa (*Ottochloa nodosa*)
  bahiagrass (*Paspalum notatum*)
  canarygrass (*Phalaris* spp.)
  foxtail (*Setaria* spp.)
  wheat (*Triticum aestivum*)
  corn (*Zea mays*)
  Perennial Broadleaves:
  mugwort (*Artemisia* spp.)
  milkweed (*Asclepias* spp.)
  canada thistle (*Cirsium arvense*)
  field bindweed (*Convolvulus arvensis*)
  kudzu (*Pueraria* spp.)
  Perennial Narrowleaves:
  brachiaria (*Brachiaria* spp.)
  bermudagrass (*Cynodon dactylon*)
  yellow nutsedge (*Cyperus esculentus*)
  purple nutsedge (*C. rotundus*)
  quackgrass (*Elymus repens*)
  lalang (*Imperata cylindrica*)
  perennial ryegrass (*Lolium perenne*)
  guineagrass (*Panicum maximum*)
  dallisgrass (*Paspalum dilatatum*)
  reed (*Phragmites* spp.)
  johnsongrass (*Sorghum halepense*)
  cattail (*Typha* spp.)
  Other Perennials:
  horsetail (*Equisetum* spp.)
  bracken (*Pteridium aquilinum*)
  blackberry (*Rubus* spp.)
  gorse (*Ulex europaeus*)

Thus, the compositions and methods of the present invention, as they pertain to glyphosate herbicide, can be useful on any of the above species.

Plants evaluated in the following Examples include the following:

| Bayer Code | Common Name |
| --- | --- |
| ABUTH | velvetleaf (*Abutilon theophrasti* Medik.) |
| CHEAL | common lambsquarters (*Chenopodium album* L.) |
| ELEIN | goosegrass (*Eleusine indica* (L.) Gaertn |
| LOLMG | annual ryegrass |
| LOLMU | Italian ryegrass (*Lolium multiflorum* Lam.) |
| LOLRI | rigid ryegrass (*Lolium rigidum*) |
| MALSI | cheeseweed |
| SINAR | wild mustard (*Sinapis arvensis* L.) |
| VIOAR | Field violet (*Viola arvensis* Murr.) |

Effectiveness in greenhouse tests, usually at exogenous chemical rates lower than those normally effective in the field, is a proven indicator of consistency of field performance at normal use rates. However, even the most promising composition sometimes fails to exhibit enhanced performance in individual greenhouse tests. As illustrated in the Examples herein, a pattern of enhancement emerges over a series of greenhouse tests; when such a pattern is identified this is strong evidence of biological enhancement that will be useful in the field.

The compositions of the present invention can be applied to plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition at the time of application to plants is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (l/ha) by spray application. The preferred application rates for aqueous solutions are in the range from about 50 to about 300 l/ha.

Many exogenous chemicals (including glyphosate herbicide) must be taken up by living tissues of the plant and translocated within the plant in order to produce the desired biological (e.g., herbicidal) effect. Thus, it is important that a herbicidal composition not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

A large number of compositions of the invention are illustrated in the Examples that follow. Many concentrate compositions of glyphosate have provided sufficient herbicidal effectiveness in greenhouse tests to warrant field testing on a wide variety of weed species under a variety of application conditions.

The field test spray compositions of ET10 contained glyphosate potassium salt or isopropylamine salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Example ET1

The efficacy of potassium glyphosate formulations containing an APG surfactant and an EAO surfactant in an APG:EAO weight ratio of 4:1 and a glyphosate a.e. to total surfactant weight ratio of about 2.9:1 were evaluated in greenhouse trials. Also evaluated were potassium glyphosate compositions containing either an alkylpolyglucoside surfactant (designated as "Surfactant L" and "Surfactant N") or an alkoxylated etheramine oxide surfactant (designated as "Surfactant G") wherein the weight ratio of glyphosate a.e. to surfactant was about 2.9:1. Finally, the efficacy of potassium glyphosate not containing a surfactant (K-GLY) and comparative compositions 139R8H and 294T6K were also evaluated. The efficacy of each formulation, surfactant and comparative composition was evaluated at application rates of 100, 200 and 400 g glyphosate a.e. per hectare. For each plant species, efficacy results are reported as the average % control for the three application rates (Table ET1A) and the calculated application rate (g a.e./ha) that must be applied to achieve 85% control (Table ET1B).

TABLE ET1a

Average % control for 100, 200 and 400 g a.e./ha application rates

| Formulation | VIOAR | SINAR | LOLMU |
|---|---|---|---|
| K-GLY | 39.2 | 67.5 | 40.8 |
| 276U4D | 52.5 | 82.5 | 52.9 |
| 902A3X | 69.2 | 79.4 | 60.0 |
| 903T6B | 62.5 | 82.1 | 62.5 |
| Surfactant G | 53.3 | 83.8 | 58.8 |
| Surfactant L | 56.7 | 81.9 | 49.2 |
| Surfactant N | 61.3 | 83.8 | 55.0 |
| Surfactants N + G (4:1 ratio) | 74.6 | 85.3 | 60.8 |
| Surfactants N + G (1:1 ratio) | 53.3 | 86.3 | 72.1 |
| Surfactants L + G (4:1 ratio) | 42.5 | 80.4 | 64.2 |
| Surfactants L + G (1:1 ratio) | 42.5 | 82.1 | 58.3 |
| 139R8H | 73.3 | 90.0 | 65.0 |
| 294T6K | 74.2 | 87.9 | 60.4 |

TABLE ET1b

Application rate (g a.e./ha) required for 85% control:

| Formulation | VIOAR | SINAR | LOLMU |
|---|---|---|---|
| K-GLY | >400.0 | >400.0 | >400.0 |
| 276U4D | 400.0 | 200.0 | >400.0 |
| 902A3X | 375.0 | 282.2 | 366.7 |
| 903T6B | >400.0 | 166.7 | 366.7 |
| Surfactant G | 400.0 | 233.3 | 323.1 |
| Surfactant L | >400.0 | 246.5 | 400.0 |
| Surfactant N | >400.0 | 250.0 | 380.0 |
| Surfactants N + G (4:1 ratio) | 327.3 | 175.0 | 375.0 |
| Surfactants N + G (1:1 ratio) | >400.0 | 171.4 | 300.0 |
| Surfactants L + G (4:1 ratio) | >400.0 | 266.7 | 360.0 |
| Surfactants L + G (1:1 ratio) | >400.0 | 228.6 | 370.0 |
| 139R8H | 325.0 | 100.0 | 323.1 |
| 294T6K | 300.0 | 154.6 | 360.0 |

Formulations containing potassium glyphosate, an APG surfactant and an EAO surfactant were more efficacious than a formulation containing potassium glyphosate, a polyoxyethylene sorbitan ester surfactant and a quaternary ammonium chloride surfactant, but less efficacious than the glyphosate IPA comparative compositions. The glyphosate compositions containing the surfactant blend of N+G appeared to provide greater efficacy that compositions container either surfactant N or surfactant G, but applied at the same total glyphosate and surfactant rate. Blends of APG and EAO surfactants provided greater efficacy than blends of AG6206 and EAO.

Example ET2

The efficacy of potassium glyphosate formulations containing various APG surfactants and an EAO surfactant in an APG:EAO weight ratios and glyphosate a.e. to total surfactant weight ratios (Gly:Surf) as indicated in the tables below. Finally, the efficacy of comparative standard compositions 139R8H and 294T6K were also evaluated. The efficacy of each formulation, surfactant and comparative composition was evaluated at application rates of 100, 200 and 400 g glyphosate a.e. per hectare. For each plant species, efficacy results are reported as the average % control for the three application rates (Table ET2a) and the calculated application rate (g a.e./ha) that must be applied to achieve 85% control (Table ET2b).

TABLE ET2a

Average % control for 100, 200 and 400 g a.e./ha application rates

| Formul. | Gly:Surf | APG:EAO | SINAR | LOLMU | ABUTH |
|---|---|---|---|---|---|
| K-GLY | — | — | 64.1 | 58.1 | 40.0 |
| 413AY6B | 2.9:1 | 4.6:1 | 84.4 | 76.6 | 47.8 |
| 413BE3M | 2.9:1 | 3.4:1 | 87.4 | 75.9 | 47.2 |
| 439AW2Z | 2.9:1 | 4.6:1 | 85.5 | 74.7 | 38.5 |
| 439BT5C | 2.9:1 | 3.4:1 | 80.6 | 74.7 | 47.2 |
| 902A3X | 2.9:1 | 4.6:1 | 79.6 | 65.0 | 53.4 |
| 903T6B | 2.9:1 | 3.4:1 | 82.8 | 72.5 | 51.3 |
| 276U4D | 1.9:1 | — | 73.4 | 61.9 | 47.2 |
| 139R8H | 2:1 | — | 85.9 | 78.1 | 69.1 |
| 294T6K | Not rept. | Not rept. | 84.7 | 77.8 | 63.3 |

TABLE ET2b

Application rate (g a.e./ha) required for 85% control

| Formulation | SINAR | LOLMU | ABUTH |
|---|---|---|---|
| K-GLY | >400.0 | >400.0 | 400.0 |
| 413AY6B | 320.0 | 316.7 | >400.0 |
| 413BE3M | 166.7 | 275.0 | >400.0 |
| 439AW2Z | 184.2 | 333.3 | >400.0 |
| 439BT5C | 283.3 | 340.0 | >400.0 |
| 902A3X | 300.0 | >400.0 | 400.0 |
| 903T6B | 194.1 | 333.3 | >400.0 |
| 276U4D | 336.7 | >400.0 | >400.0 |
| 139R8H | 300.0 | 266.7 | 280.0 |
| 294T6K | 240.0 | 357.1 | 357.1 |

The 413 and 439 series formulations and formulation 903T6B provided equal or superior control to that of comparative standard 276U4D. 413AY6B and 439AW2Z were more efficacious than 902A3X on SINAR and LOLMU. 413BE3M and 439BT5C were of similar efficacy as 903T6B.

Example ET3

The efficacy of potassium glyphosate formulations containing various ratios of APG surfactants to EAO surfactants were evaluated in greenhouse trials as compared to comparative compositions 139R8H, 276U4D and K-GLY. The efficacy of each formulation, surfactant and comparative composition was evaluated at application rates of 100, 200 and 400 g glyphosate a.e. per hectare and the results are reported in Table ET3A wherein APG:EAO is the weight ratio of APG surfactant to EAO surfactant and Gly:Surf is the weight ratio of glyphosate a.e. to total surfactant. For each plant species, efficacy results are reported as the average % control for the three application rates (Table ET3a) and the calculated application rate (g a.e./ha) that must be applied to achieve 85% control (Table ET3b).

TABLE ET3a

Average % control for 100, 200 and 400 g a.e./ha application rates

| Formulation | Gly:Surf | APG:EAO | CHEAL | VIOAR | LOLMU |
|---|---|---|---|---|---|
| K-GLY | — | — | 5.0 | 27.5 | 27.9 |
| 847A6D | 3:1 | 3.2:1 | 43.8 | 28.3 | 35.8 |
| 850A4S | 2.9:1 | 3.4:1 | 58.8 | 33.3 | 47.5 |
| 901AB7Y | 3.8:1 | 3.2:1 | 37.1 | 33.3 | 38.8 |
| 901BT6H | 4.5:1 | 3.2:1 | 33.3 | 33.3 | 35.8 |
| 901CW2R | 2.9:1 | 4.6:1 | 61.3 | 31.7 | 46.3 |
| 901DV8U | 2.9:1 | 6.6:1 | 51.8 | 35.8 | 40.4 |
| 901ER2P | 2.8:1 | 3.6:1 | 49.2 | 35.8 | 41.3 |
| 901FT6J | 3:1 | 3.3:1 | 48.8 | 31.7 | 51.3 |
| 919AS3M | 3:1 | 3.9:1 | 36.3 | 35.0 | 39.6 |
| 919BT8J | 3:1 | 4.3:1 | 33.3 | 34.6 | 38.8 |
| 919CP0K | 2.9:1 | 4.2:1 | 61.3 | 34.2 | 52.1 |
| 919DE7G | 2.9:1 | 4.6:1 | 45.4 | 41.7 | 45.4 |
| 276U4D | 1.9:1 | — | 61.4 | 44.2 | 65.4 |
| 139R8H | 2:1 | — | 67.5 | 43.3 | 60.8 |

TABLE ET3b

Application rate (g a.e./ha) required for 85% control

| Formulation | CHEAL | VIOAR | LOLMU |
|---|---|---|---|
| K-GLY | >400.0 | >400.0 | >400.0 |
| 847A6D | 371.4 | >400.0 | >400.0 |
| 850A4S | 341.2 | >400.0 | >400.0 |
| 901AB7Y | 389.1 | >400.0 | >400.0 |
| 901BT6H | 400.0 | >400.0 | >400.0 |
| 901CW2R | 305.9 | >400.0 | >400.0 |
| 901DV8U | 400.0 | >400.0 | >400.0 |
| 901ER2P | 352.9 | >400.0 | >400.0 |
| 901FT6J | 373.0 | >400.0 | >400.0 |
| 919AS3M | >400.0 | >400.0 | >400.0 |
| 919BT8J | 400.0 | >400.0 | >400.0 |
| 919CP0K | 294.7 | >400.0 | >400.0 |
| 919DE7G | 377.1 | >400.0 | >400.0 |
| 276U4D | 328.0 | 400.0 | 352.4 |
| 139R8H | 266.7 | >400.0 | 377.8 |

All experimental formulations were less efficacious than comparative formulations 276U4D and 139R8H. Generally, formulations containing PG 2067 were more efficacious than those containing AG 6206. Three-way combinations of EAO, PG 2067 and AG 6206 were less efficacious than formulations containing EAO and PG 2067.

Example ET4

The efficacy of potassium glyphosate formulations containing various ratios of APG surfactants to EAO surfactants were evaluated in greenhouse trials as compared to comparative compositions 139R8H and 276U4D. The efficacy of each formulation, surfactant and comparative composition was evaluated at application rates of 200, 400 and 600 g glyphosate a.e. per hectare and the results are reported in Table ET4A wherein APG:EAO is the weight ratio of APG surfactant to EAO surfactant and Gly:Surf is the weight ratio of glyphosate a.e. to total surfactant. For each plant species, efficacy results are reported as the average % control for the three application rates (Table ET4a) and the calculated application rate (g a.e./ha) that must be applied to achieve 85% control (Table ET4b).

TABLE ET4a

Average % control for 200, 400 and 600 g a.e./ha application rates

| Formul. | Gly:Surf | APG:EAO | MALSI | LOLRI | VIOAR | SINAR |
|---|---|---|---|---|---|---|
| 836Y7G | 1.9:1 | — | 32.1 | 41.7 | 38.3 | 74.1 |
| 838I6T | 1.6:1 | — | 47.1 | 39.2 | 55.0 | 80.0 |
| 847A6D | 3:1 | 3.2:1 | 45.8 | 46.7 | 49.6 | 70.8 |
| 847B4K | 3.1:1 | 2.5:1 | 41.7 | 29.2 | 41.7 | 70.0 |
| 847C7L | 3.1:1 | 3.2:1 | 37.5 | 40.8 | 47.5 | 68.8 |
| 850A4S | 2.9:1 | 3.4:1 | 57.1 | 47.1 | 30.8 | 78.3 |
| 276U4D | 1.9:1 | — | 47.5 | 44.6 | 51.7 | 62.1 |
| 139R8H | 2:1 | — | 61.3 | 53.3 | 60.4 | 71.3 |

TABLE ET4b

Application rate (g a.e./ha) required for 85% control

| Formulation | MALSI | LOLRI | VIOAR | SINAR |
|---|---|---|---|---|
| 836Y7G | >600 | >600 | >600 | >600 |
| 838I6T | >600 | >600 | >600 | 488.9 |
| 847A6D | >600 | >600 | >600 | 571.4 |
| 847B4K | >600 | >600 | >600 | >600 |
| 847C7L | >600 | >600 | >600 | >600 |
| 850A4S | >600 | >600 | >600 | 533.3 |
| 276U4D | >600 | >600 | >600 | >600 |
| 139R8H | >600 | >600 | >600 | >600 |

Overall, 850A4S (AG 6206 and Tomah AO 17-7) and 847A6D (Agrimul PG 2067 and Tomah AO 17-7) were less efficacious than comparative standard 139R8H, but more efficacious than standard 276U4D. On SINAR, 850A4S, 836Y7G and 838I6T were more efficacious, and 847A6D was slightly less efficacious than comparative standard 139R8H. All experimental formulations provided better SINAR control than comparative standard 276U4D. On MALSI, 139R9H gave the greatest control and 850A4S was more efficacious than standard 276U4D. On VIOAR, 139R8H was the most efficacious formulation, while 838I6T was more efficacious than 276U4D. On LOLRI, 850A4S and 847A6D were less efficacious than 139R8H, but more efficacious than 276U4D.

Example ET5

The efficacy of potassium glyphosate formulations containing Atplus 452 and EAO surfactants were evaluated in greenhouse trials. The efficacy of each formulation, surfactant and comparative composition was evaluated at application rates of 100, 200, 300 and 400 g glyphosate a.e. per hectare and the results are reported in Table ET5A wherein APG:EAO is the weight ratio of APG surfactant to EAO surfactant and Gly:Surf is the weight ratio of glyphosate a.e. to total surfactant. For each plant species, efficacy results are reported as the average % control for the three application rates (Table ET5a) and the calculated application rate (g a.e./ha) that must be applied to achieve 85% control (Table ET5b).

TABLE ET5a

Average % control for 100, 200, 300 and 400 g a.e./ha application rates

| Formul. | Gly:Surf | APG:EAO | VIOAR | SINAR | LOLMG |
|---|---|---|---|---|---|
| K-GLY | — | — | 34.7 | 72.5 | 42.5 |
| 413AY6B | 2.9:1 | 4.6:1 | 49.7 | 82.8 | 80.9 |
| 413BE3M | 2.9:1 | 3.4:1 | 50.0 | 84.8 | 78.8 |
| 294W6S | 5:1 | — | 71.3 | 87.2 | 81.9 |
| 902A3X | 2.9:1 | 4.6:1 | 56.9 | 84.1 | 77.5 |
| 903T6B | 2.9:1 | 3.1:1 | 55.3 | 83.8 | 78.3 |
| 276U4D | 1.9:1 | — | 58.4 | 86.1 | 83.1 |
| 139R8H | 2:1 | — | 77.5 | 90.0 | 85.9 |

TABLE ET5b

Application rate (g a.e./ha) required for 85% control

| Formulation | VIOAR | SINAR | LOLMG |
|---|---|---|---|
| K-GLY | >400.0 | 366.7 | >400.0 |
| 413AY6B | >400.0 | 266.7 | 233.3 |
| 413BE3M | 400.0 | 233.3 | 300.0 |
| 294W6S | 358.3 | 166.7 | 266.7 |
| 902A3X | 375.0 | 200.0 | 266.7 |
| 903T6B | 377.8 | 275.0 | 266.7 |
| 276U4D | 366.7 | 200.0 | 250.0 |
| 139R8H | 250.0 | 175.0 | 188.2 |

Overall, the efficacy of 902A3X and 903T6B was similar to standard 276U4D, and 902A3X was slightly more efficacious than 903T6B. Formulations containing PG 2067 were slightly more efficacious on VIOAR than formulations containing Atplus 452.

Example ET6

The efficacy of potassium glyphosate formulations containing an APG surfactant and an EAO surfactant were evaluated in greenhouse trials. Formulation 307D5R contained surfactant G (Tomah AO-17-7), formulation 307E4S contained surfactant N (Agrimul PG-2067), and formulation 307F3T contained surfactant L (Akzo-Nobel AG-6206). The efficacy of comparative compositions 139R8H and 294T6K were also evaluated. The efficacy of each formulation, surfactant and comparative composition was evaluated at application rates of 200, 400 and 600 g glyphosate a.e. per hectare and the results are reported in Table ET6A wherein APG:EAO is the weight ratio of APG surfactant to EAO surfactant and Gly:Surf is the weight ratio of glyphosate a.e. to total surfactant. For each plant species, efficacy results are reported as the average % control for the three application rates and the calculated application rate (g a.e./ha) that must be applied to achieve 85% control (Table ET6).

TABLE ET6

Average % control for 200, 400 and 600 g a.e./ha application rates and application rate for 85% control

| Form. | Gly:Surf | APG:EAO | CHEAL (ave. cntrl) | CHEAL (g a.e./ha for 85% control) | VIOAR (ave. cntrl) | VIOAR (g a.e./ha for 85% control) |
|---|---|---|---|---|---|---|
| K-GLY | — | — | 33.3 | >600.0 | 31.7 | >600.0 |
| 307D5R | 4:1 | — | 70.4 | 415.4 | 72.5 | >600.0 |
| 307E4S | 4:1 | — | 75.8 | 525.0 | 64.6 | >600.0 |
| 307F3T | 4:1 | — | 64.2 | 600.0 | 58.3 | 560.0 |
| 847A6D | 3:1 | 3.2:1 | 60.8 | 538.5 | 51.7 | >600.0 |
| 850A4S | 2.9:1 | 3.4:1 | 63.8 | 560.0 | 58.3 | >600.0 |
| 276U4D | 1.9:1 | — | 72.5 | 560.0 | 59.2 | >600.0 |
| 139R8H | 2:1 | — | 84.6 | 433.3 | 72.5 | 571.4 |

Overall, formulations 307D5R and 307E4S had the highest efficacy. EAO tank mixed with the Tween 20 equivalent was less efficacious than 276U4D but more efficacious than 847A6D and 850A4S. Formulation 850A4S was more efficacious than formulation 847A6D.

Example ET7

The effect of antifoam on the efficacy of potassium glyphosate formulations containing the combination of an APG and an EAO surfactant was evaluated in greenhouse testing. The efficacy of each formulation and comparative composition was evaluated at application rates of 50, 100 and 300 g glyphosate a.e. per hectare and the results are reported in Table ET7A wherein APG:EAO is the weight ratio of alkylpolyglucoside (APG) surfactant to alkoxylated amine oxide (EAO) surfactant and Gly:Surf is the weight ratio of glyphosate a.e. to total surfactant. For each plant species, efficacy results are reported as the average % control for the three application rates and the calculated application rate (g a.e./ha) that must be applied to achieve 85% control (Table ET10a).

TABLE ET7

Average % control for 50, 100 and 300 g a.e./ha application rates and application rate for 85% control

| Form. | Gly:Surf | APG:EAO | SINAR 10 DAT (ave. Ctrl) | SINAR 10 DAT (g a.e./ha for 85% control) | LOLMU 23 DAT (ave. control) | LOLMU 23 DAT (g a.e./ha for 85% control) |
|---|---|---|---|---|---|---|
| K-GLY | — | — | 74.6 | 227.3 | 48.3 | >300.0 |
| 447A7P | 5:1 | — | 78.8 | 300.0 | 66.7 | 288.9 |
| 447B0I | 5:1 | — | 85.4 | 120.0 | 69.2 | 271.4 |
| 447C3Z | 5:1 | — | 83.3 | 176.0 | 67.5 | 280.0 |

TABLE ET7-continued

Average % control for 50, 100 and 300 g a.e./ha application rates and application rate for 85% control

| Form. | Gly:Surf | APG:EAO | SINAR 10 DAT (ave. Ctrl) | SINAR 10 DAT (g a.e./ha for 85% control) | LOLMU 23 DAT (ave. control) | LOLMU 23 DAT (g a.e./ha for 85% control) |
|---|---|---|---|---|---|---|
| 458A6T | 2.9:1 | 4.6:1 | 78.3 | 300.0 | 58.8 | >300.0 |
| 458B5N | 2.9:1 | 4.6:1 | 77.9 | 300.0 | 60.4 | >300.0 |
| 459A5E | 2.9:1 | 3.4:1 | 78.4 | 223.5 | 57.9 | >300.0 |
| 459B2Y | 2.9:1 | 3.4:1 | 78.8 | 200.0 | 65.4 | 284.6 |
| 902A3X | 2.9:1 | 4.6:1 | 84.5 | 140.8 | 57.1 | >300.0 |
| 903T6B | 2.9:1 | 3.4:1 | 77.5 | 233.3 | 62.5 | 300.0 |
| 276U4D | 1.9:1 | — | 81.1 | 188.2 | 55.8 | >300.0 |
| 139R8H | 2:1 | — | 85.8 | 100.0 | 71.3 | 277.8 |
| 294T6K | Not rept. | Not rept. | 80.0 | 200.0 | 65.8 | >300.0 |

The addition of antifoam 1-3 effectively reduced foaming of the stock solutions prepared for spraying and did not affect efficacy. Overall, 902A3X and 903T6B had similar efficacy to 276U4D.

Example ET8

The effect of aging compositions of the present invention at an elevated temperature of 40° C. for 8 weeks on the efficacy of potassium glyphosate formulations containing the combination of an APG and an EAO surfactant was evaluated in greenhouse testing. The efficacy of each formulation and comparative composition was evaluated at application rates of 50, 100 and 300 g glyphosate a.e. per hectare and the results are reported in Table ET8A wherein APG:EAO is the weight ratio of alkylpolyglucoside (APG) surfactant to alkoxylated amine oxide (EAO) surfactant and Gly:Surf is the weight ratio of glyphosate a.e. to total surfactant. For each plant species, efficacy results are reported as the average % control for the three application rates (Table ET8a) and the calculated application rate (g a.e./ha) that must be applied to achieve 85% control (Table ET8b).

TABLE ET8a

Average % control for 50, 100 and 300 g a.e./ha application rates

| Formulation | Gly:Surf | APG:EAO | VIOAR | SINAR | LOLMU |
|---|---|---|---|---|---|
| 919AS3M | 3:1 | 3.9:1 | 32.1 | 71.3 | 63.3 |
| 919AS3M[a] | 3:1 | 3.9:1 | 34.2 | 70.8 | 55.8 |
| 919BT8J | 3:1 | 4.3:1 | 32.1 | 66.7 | 56.3 |
| 919BT8J[a] | 3:1 | 4.3:1 | 29.2 | 76.7 | 48.3 |
| 919CP0K | 2.9:1 | 4.2:1 | 35.0 | 57.5 | 58.3 |
| 919CP0K[a] | 2.9:1 | 4.2:1 | 30.4 | 70.0 | 56.3 |
| 919DE7G | 2.9:1 | 4.6:1 | 29.2 | 74.2 | 56.7 |
| 919DE7G[a] | 2.9:1 | 4.6:1 | 32.5 | 75.8 | 61.7 |
| 847A6D | 3:1 | 3.2:1 | 26.7 | 78.3 | 57.9 |
| 847A6D[a] | 3:1 | 3.2:1 | 34.2 | 67.9 | 62.1 |
| 850A4S | 2.9:1 | 3.4:1 | 43.3 | 70.8 | 57.1 |
| 850A4S[a] | 2.9:1 | 3.4:1 | 31.7 | 80.4 | 52.5 |
| 276U4D | 1.9:1 | — | 37.5 | 68.8 | 58.8 |
| 139R8H | 2:1 | — | 43.3 | 80.4 | 73.3 |

[a]Aged for 8 weeks at 40° C. before efficacy testing.

TABLE ET8b

Application rate (g a.e./ha) required for 85% control

| Formulation | VIOAR | SINAR | LOLMU |
|---|---|---|---|
| 919AS3M | >300.0 | 300.0 | 250.0 |
| 919AS3M[a] | >300.0 | 233.3 | >300.0 |
| 919BT8J | >300.0 | 275.0 | >300.0 |
| 919BT8J[a] | >300.0 | 233.3 | >300.0 |
| 919CP0K | >300.0 | 260.0 | 233.3 |
| 919CP0K[a] | >300.0 | 250.0 | 292.6 |
| 919DE7G | >300.0 | >300.0 | 260.0 |
| 919DE7G[a] | >300.0 | 300 | >300.0 |
| 847A6D | >300.0 | 200.0 | >300.0 |
| 847A6D[a] | >300.0 | 300.0 | 245.5 |
| 850A4S | >300.0 | 300.0 | >300.0 |
| 850A4S[a] | >300.0 | 233.3 | 300.0 |
| 276U4D | >300.0 | >300.0 | 256.5 |
| 139R8H | >300.0 | 225.0 | 140.0 |

[a]Aged for 8 weeks at 40° C. before efficacy testing.

Overall, only slight differences in efficacy between freshly prepared and 8 week-old samples were found, and aging at elevated temperature does not appear to impact efficacy.

Example ET9

The efficacy of formulations containing potassium glyphosate and an APG surfactant (formulation 179W2N) or an EAO surfactant (formulation 179R6U) in a weight percent ratio of glyphosate a.e. to surfactant of 4:1 was evaluated in greenhouse trials as compared to compositions 276U4D, 351L9P, 294T6K and K-GLY. The efficacy of each formulation, surfactant and comparative composition was evaluated at application rates of 100, 200 and 400 g glyphosate a.e. per hectare and the results are reported in Table ET8A wherein APG:EAO is the weight ratio of alkylpolyglucoside (APG) surfactant to alkoxylated amine oxide (EAO) surfactant and Gly:Surf is the weight ratio of glyphosate a.e. to total surfactant. For each plant species, efficacy results are reported as the average % control for the three application rates (Table ET9).

TABLE ET9

Average % control for 100, 200 and 400 g a.e./ha application rates

| Formulation | Gly:Surf | APG:EAO | VIOAR | LOLMG | MALSI | ABUTH |
|---|---|---|---|---|---|---|
| K-GLY | — | — | 36.7 | 37.8 | 22.8 | 27.2 |
| 179R6U (EAO) | 4:1 | — | 69.4 | 66.1 | 57.2 | 39.4 |
| 179W2N (APG) | 4:1 | — | 64.2 | 46.9 | 53.3 | 32.8 |
| 351L9P | 2.9:1 | 4.6:1 | 67.8 | 60.8 | 52.8 | 35.6 |
| 294T6K | Not Rept | No Rept | 64.4 | 60.3 | 53.3 | 37.8 |
| 276U4D | 1.9:1 | — | 63.1 | 60.0 | 48.1 | 36.9 |

Differences in efficacy due to surfactant were very small on broadleaf species with only LOLMG showing significant differences. The EAO surfactant in combination with potassium glyphosate gave the highest level of efficacy. LOLMG and ABUTH results indicate that the APG in combination with potassium glyphosate is less efficacious than the standards.

Example ET10

The efficacy of formulations 902A3X and 903T6B on ELEIN at 10 and 23 days after treatment ("DAT") was evaluated compared to standards 276U4D and 294T6K in field trials done in Jefferson County, Missouri, USA. The efficacy of each formulation and comparative composition was evaluated at application rates of 200, 400 and 600 g glyphosate a.e. per hectare. For each plant species, efficacy results are reported as the average % control for the three application rates and the calculated application rate (g a.e./ha) that must be applied to achieve 85% control (Table ET10a).

TABLE ET10a

Average % control for 200, 400 and 600 g a.e./ha application rates and application rate for 85% control

| Form. | ELEIN 10DAT (ave. control) | ELEIN 10DAT (g a.e./ha for 85% control) | ELEIN 23DAT (ave. control) | ELEIN 23DAT (g a.e./ha for 85% control) |
|---|---|---|---|---|
| 902A3X | 51.1 | >600.0 | 79.0 | 368.1 |
| 903T6B | 55.4 | >600.0 | 69.8 | 502.9 |
| 276U4D | 53.3 | >600.0 | 75.1 | 427.8 |
| 294T6K | 59.4 | >600.0 | 78.2 | 432.6 |

Overall, no statistical difference among the formulations and the standards was observed.

Toxicity Testing

Compositions of the present invention and prior art compositions, containing the ingredients listed in Table TT1 below, were evaluated for toxicity according to the following method.

As indicated in Table TT1, compositions having the indicated percent active component content were prepared from a potassium glyphosate solution containing about 47.2 wt. % a.e. potassium glyphosate ("K-gly"), and surfactant components selected from Agrimul PG 2067 surfactant ("APG 2067", about 70 percent active content—previously described), Genamin C-050 surfactant ("GC-050", about 100 percent polyoxyethylene(5)cocoamine surfactant—Clariant), Genamin T-050 surfactant ("GT-050", about 100 percent polyoxyethylene(5)tallowamine surfactant—Clariant), Tomah AO-17-7 surfactant ("AO-17-7", about 80 percent active component—previously described), Synergen PE surfactant ("PE", about 100 percent polyoxyethylene(5) isotridecyloxypropylamine surfactant—Clariant), Ethomeen T/25 surfactant ("T25", about 70 percent polyoxyethylene (15)tallowamine surfactant—Akzo) and deionized water. Also shown in Table TT1 are the weight ratios of APG 2067 surfactant to cosurfactant and glyphosate (a.e.) to total surfactant. Comparative compositions 1 and 2 ("Compar. 1" and "Compar. 2") were prior art compositions containing APG 2067 surfactant in combination with an alkylamine ethoxylate surfactant at weight ratios of APG to alkylamine ethoxylate of 2.6:1 and 2.7:1, respectively, and weight ratios of glyphosate (a.e.) to total surfactant of 3:1 and 2.4:1, respectively. Comparative compositions 3 and 4 comprised glyphosate in combination with PE and T25 surfactants, respectively, in the absence of APG surfactant. Formulations 1-4 represent compositions of the present invention. Formulation 1 ("Form") was formulated similarly to Compar. 1, but the GC-050 surfactant was replaced with AO-17-7 surfactant. Form. 2 was formulated similarly to Compar. 2, but the GT-050 surfactant was replaced with AO-17-7 surfactant.

TABLE TT1

| Component | Compar. 1 | Compar. 2 | Compar. 3 | Compar. 4 |
|---|---|---|---|---|
| K-gly (g a.e./L) | 36.9 | 33.8 | 20 | 20 |
| APG 2067 (wt % a.i.) | 8.9 | 10.4 | — | — |
| GC-050 (wt % a.i.) | 3.4 | — | — | — |
| GT-050 (wt % a.i.) | — | 3.8 | — | — |
| AO-17-7 (wt % a.i.) | — | — | — | — |
| PE (wt % a.i.) | — | — | 5 | — |
| T25 (wt % a.i.) | — | — | — | 5 |
| APG:Cosurf | 2.6:1 | 2.7:1 | — | — |
| Gly:Surf | 3:1 | 2.4:1 | 4:1 | 4:1 |

| Component | Form. 1 | Form. 2 | Form. 3 | Form. 4 |
|---|---|---|---|---|
| K-gly (g a.e./L) | 36.9 | 33.8 | 35.8 | 20 |
| APG 2067 (wt % a.i.) | 8.9 | 10.4 | 7.2 | 4 |
| GC-050 (wt % a.i.) | — | — | — | — |
| GT-050 (wt % a.i.) | — | — | — | — |
| AO-17-7 (wt % a.i.) | 3.4 | 3.8 | 1.8 | 1 |
| APG:Cosurf | 2.6:1 | 2.7:1 | 4:1 | 4:1 |
| Gly:Surf | 3:1 | 2.4:1 | 4:1 | 4:1 |

The Table TT1 compositions were evaluated for aquatic toxicity using a *Daphnia* acute toxicity assay in a miniaturized test system following the methodology of Powell et al. (see Powell R. L., Moser E. M., Kimerle R. A., McKenzie D. E., McKee M. 1996, *Use of a miniaturized test system for determining acute toxicity of toxicity identification evaluation fractions*, Ecotoxicol Environ Saf., 1996 Oct, 35(1):1-6) using a miniaturized test system comprising exposing test organisms in 1 ml of test solution using 48-well microtiter plates for the test vessels. The percent mortality results for each concentration (nominal concentration in mg/L) are reported along with an $EC_{50}$ (estimated using binomial probability (i.e., nonlinear interpolation)) for each composition in Tables TT2 and TT3 below.

TABLE TT2

| | Percent Mortality | | | | |
|---|---|---|---|---|---|
| mg/L | Compar. 1 | Form. 1 | Compar. 2 | Form. 2 | Form. 3 |
| 0 | 0 | 0 | 0 | 0 | 0 |
| 81 | 0 | 0 | 0 | 0 | — |
| 130 | 100 | 0 | 100 | 10 | 0 |
| 216 | 100 | 0 | 100 | 90 | 0 |
| 360 | 100 | 90 | 100 | 100 | 30 |
| 600 | 100 | 100 | 100 | 100 | 80 |
| 1000 | 100 | 100 | 100 | 100 | 100 |
| $EC_{50}$ = | <81 mg/L | 294 mg/L | <81 mg/L | 168 mg/L | 440 mg/L |

TABLE TT3

| | Percent Mortality | | | |
|---|---|---|---|---|
| mg/L | Compar. 3 | Compar. 4 | Form. 3. | Form. 4 |
| 0 | 0 | 0 | 0 | 0 |
| 28 | 0 | 30 | not tested | not tested |
| 47 | 0 | 80 | not tested | not tested |
| 78 | 10 | 100 | not tested | not tested |
| 81 | not tested | not tested | not tested | not tested |
| 130 | 50 | 100 | 0 | not tested |

TABLE TT3-continued

| | Percent Mortality | | | |
|---|---|---|---|---|
| mg/L | Compar. 3 | Compar. 4 | Form 3. | Form. 4 |
| 216 | 100 | 100 | 0 | 0 |
| 360 | 100 | 100 | 40 | 0 |
| 600 | not tested | not tested | 60 | 60 |
| 1000 | not tested | not tested | 100 | 80 |
| 1600 | not tested | not tested | not tested | 90 |
| $EC_{50}$ = | 130 mg/L | 34 mg/L | 465 mg/L | 562 mg/L |

The assay results reproduced in Tables TT2 and TT3 were conducted within a few weeks of one another, used the same methodology, and were conducted at the same laboratory with the same culture of *Daphnia*. The EC50 values for the assays for Formulation 3, performed on different days and reported in Tables TT2 and TT3, provide nearly identical $EC_{50}$ values, which demonstrates the reproducibility of the assay method. The assay results clearly indicate significantly lower toxicity for the compositions of the present invention versus the prior art and comparative compositions.

A composition of the present invention, Formulation 5, containing 35.9 wt % a.e. potassium glyphosate, 6.7 wt % a.i. APG 2067 and 2.2 wt % a.i. AO-17-7 was evaluated for toxicity according to EEC Method C.2 (1992); OECD 202 (1984). The 48-hour water flea (*Daphnia magna*) toxicity of Form. 5 was determined in a static system. Four groups of five daphnids each (less than 24 hours old) were exposed in filtered well water for two days to Form. 5 at nominal concentrations of 0 (control), 63, 125, 250, 500, and 1000 mg/L. The daphnids were kept on a 16-hour:8-hour light:dark regimen and were not fed during the exposure period. Immobilisation was assessed at 5, 24, and 48 hours after test initiation. Temperature, pH and dissolved oxygen concentrations were recorded at 0 and 48 hours in one replicate of each treatment level, including controls. Total hardness and alkalinity of the dilution medium were measured before use. At 0 and 48 hours, samples of test medium were taken for quantification of glyphosate acid by HPLC.

Immobilization data for the control and treated groups are reported in Table TT4. During the test, water temperature ranged from 19.2 to 20.7° C. in individual replicates and from 19.5 to 20.5° C. by continuous monitoring, The pH ranged from 6.7 to 8.6, and dissolved oxygen concentrations ranged from 9.4 to 9.1 mg/L (5.1 mg/L=60% saturation at 20° C.). Total hardness and alkalinity of the test water were 136 and 184 mg $CaCO_3$/L, respectively, at test initiation. The mean measured concentrations of Form. 5 were 63, 127, 256, 504, and 1021 mg/L (100, 102, 102, 101, and 102% of nominal concentrations, respectively). Results were expressed based on mean measured concentrations.

TABLE TT4

| Conc. (mean) mg/L | Time (h) | Abnormal/Sublethal effects[1] | Immobili.[2] | Cumulative Mortality % |
|---|---|---|---|---|
| 0 | 5 | none observed | 0/20 | |
| 0 | 24 | none observed | 0/20 | |
| 0 | 48 | none observed | 0/20 | 0 |
| 63 (63) | 5 | none observed | 0/20 | |
| 63 (63) | 24 | none observed | 0/20 | |
| 63 (63) | 48 | none observed | 0/20 | 0 |
| 125 (127) | 5 | none observed | 0/20 | |
| 125 (127) | 24 | none observed | 0/20 | |
| 125 (127) | 48 | none observed | 0/20 | 0 |
| 250 (256) | 5 | 20 AN | 0/20 | |

TABLE TT4-continued

| Conc. (mean) mg/L | Time (h) | Abnormal/Sublethal effects[1] | Immobili.[2] | Cumulative Mortality % |
|---|---|---|---|---|
| 250 (256) | 24 | 20 AN | 0/20 | |
| 250 (256) | 48 | 4 L | 16/20 | 80 |
| 500 (504) | 5 | 20 AN | 0/20 | |
| 500 (504) | 24 | 15 AN | 5/20 | |
| 500 (504) | 48 | 1 L | 19/20 | 95 |
| 1000 (1021) | 5 | 20 AN | 0/20 | |
| 1000 (1021) | 24 | 16 AN | 4/20 | |
| 1000 (1021) | 48 | 1 L | 19/20 | 95 |

[1]L—lethargic; AN—appear normal
[2]Number of immobilised and dead individuals/total number of daphnids in the group.

Based on mean measured concentrations, the 48-hour $EC_{50}$ value for *Daphnia magna* exposed to Form. 5 in a static system was 243 mg/L (95% confidence interval: 188-311 mg/L). The no-observed-effect-concentration (NOEC) was determined to be 127 mg Form. 5/L.

Comparative compositions 1-4 and Formulations 1-4 were tested for *Daphnia magna* toxicity in a static screening test according to EEC Method C.2 (1992); OECD 202 (1984) referenced above. The results are presented in Tables TT5-TT13 below wherein "common control" refers to an evaluation performed in the absence of an added comparative composition or formulation of the present invention.

TABLE TT5

Comparative composition 1

| | Number Dead/Number Immobile/ Number Exposed (Observations)[1] | | Cumulative |
|---|---|---|---|
| Conc. (mg/L) | 24 Hours | 48 Hours | % Mortality |
| Common Control | 0/0/20 (20 AN) | 0/0/20 (20 AN) | 0 |
| 81 | 0/10/10 (N/R) | 9/1/10 (N/R) | 100 |
| 130 | 0/10/10 (N/R) | 10/0/10 (N/R) | 100 |
| 216 | 6/4/10 (N/R) | 10/0/10 (N/R) | 100 |
| 360 | 10/0/10 (N/R) | 10/0/10 (N/R) | 100 |
| 600 | 10/0/10 (N/R) | 10/0/10 (N/R) | 100 |
| 1000 | 10/0/10 (N/R) | 10/0/10 (N/R) | 100 |

[1]Observations: AN = Appeared Normal; N/R = not reported

Water chemistry parameters: Temperature at time (0)=18.6° C.; Temperature at time (48 hours)=20.1° C. Dissolved oxygen ranged from 8.7-9.1 ppm in all treatment groups. At test initiation, the pH was 6.7 in the 1000 mg/L treatment group and the pH ranged from 7.8 to 8.4 in all treatment groups at 24 and 48 hours.

TABLE TT6

Comparative composition 2

| | Number Dead/Number Immobile/ Number Exposed (Observations)[1] | | Cumulative |
|---|---|---|---|
| Conc. (mg/L) | 24 Hours | 48 Hours | % Mortality |
| Common Control | 0/0/20 (20 AN) | 0/0/20 (20 AN) | 0 |
| 81 | 0/9/10 (1L) | 9/1/10 (N/R) | 100 |
| 130 | 0/10/10 (N/R) | 10/0/10 (N/R) | 100 |
| 216 | 7/3/10 (N/R) | 10/0/10 (N/R) | 100 |
| 360 | 10/0/10 (N/R) | 10/0/10 (N/R) | 100 |
| 600 | 10/0/10 (N/R) | 10/0/10 (N/R) | 100 |
| 1000 | 10/0/10 (N/R) | 10/0/10 (N/R) | 100 |

[1]Observations: AN = Appeared Normal; L = lethargic; N/R = not reported

Water chemistry parameters: Temperature at time (0)=18.6° C.; Temperature at time (48 hours)=20.1° C. Dissolved oxygen ranged from 8.7-9.1 ppm in all treatment groups. At test initiation, the pH was 6.7 in the 1000 mg/L treatment group and the pH ranged from 7.8 to 8.4 in all treatment groups at 24 and 48 hours.

TABLE TT7

Comparative composition 3

| Conc. (mg/L) | Number Dead/Number Immobile/ Number Exposed (Observations)[1] | | Cumulative % Mortality |
|---|---|---|---|
| | 24 Hours | 48 Hours | |
| Common Control | 0/0/20 (20 AN) | 0/0/20 (20 AN) | 0 |
| 28 | 0/0/10 (10 AN) | 0/0/10 (10 AN) | 0 |
| 47 | 0/0/10 (10 AN) | 0/0/10 (10 AN) | 0 |
| 78 | 0/0/10 (10 AN) | 1/0/10 (5 AN; 4 L) | 10 |
| 130 | 0/0/10 (10 AN) | 2/3/10 (5 L) | 50 |
| 216 | 0/5/10 (5 L) | 10/0/10 (N/R) | 100 |
| 360 | 9/0/10 (1 L) | 10/0/10 (N/R) | 100 |

[1]Observations: AN = Appeared Normal; L = lethargic; N/R = not reported

Water chemistry parameters: Temperature at time (0)=19.5° C.; Temperature at time (48 hours)=20.0° C. Dissolved oxygen ranged from 8.3-8.5 ppm in all treatment groups. At test initiation, the pH was 7.5 in the 360 mg/L treatment group and the pH ranged from 8.3 to 8.6 in all treatment groups at 24 and 48 hours.

TABLE TT8

Comparative composition 4

| Conc. (mg/L) | Number Dead/Number Immobile/ Number Exposed (Observations)[1] | | Cumulative % Mortality |
|---|---|---|---|
| | 24 Hours | 48 Hours | |
| Common Control | 0/0/20 (20 AN) | 0/0/20 (20 AN) | 0 |
| 28 | 0/0/10 (10 AN) | 0/3/10 (7 AN) | 30 |
| 47 | 0/0/10 (10 AN) | 8/2/10 (N/R) | 80 |
| 78 | 3/2/10 (5 L) | 10/0/10 (N/R) | 100 |
| 130 | 4/0/10 (1 AN; 5 L) | 10/0/10 (N/R) | 100 |
| 216 | 5/0/10 (1 AN; 4 L) | 10/0/10 (N/R) | 100 |
| 360 | 9/0/10 (1 L) | 10/0/10 (N/R) | 100 |

[1]Observations: AN = Appeared Normal; L = lethargic; N/R = not reported

Water chemistry parameters: Temperature at time (0)=19.5° C.; Temperature at time (48 hours)=20.0° C. Dissolved oxygen ranged from 8.3-8.6 ppm in all treatment groups. At test initiation, the pH was 7.5 in the 360 mg/L treatment group and the pH ranged from 8.3 to 8.6 in all treatment groups at 24 and 48 hours.

TABLE TT9

Formulation 1

| Conc. (mg/L) | Number Dead/Number Immobile/ Number Exposed (Observations)[1] | | Cumulative % Mortality |
|---|---|---|---|
| | 24 Hours | 48 Hours | |
| Common Control | 0/0/20 (20 AN) | 0/0/20 (20 AN) | 0 |
| 81 | 0/0/10 (10 AN) | 0/0/10 (10 AN) | 0 |
| 130 | 0/0/10 (10 AN) | 0/0/10 (10 AN) | 0 |
| 216 | 0/0/10 (10 AN) | 0/0/10 (10 AN) | 0 |
| 360 | 0/2/10 (8 AN) | 6/3/10 (1 L) | 90 |
| 600 | 6/0/10 (4 L) | 10/0/10 (N/R) | 100 |
| 1000 | 5/0/10 (5 L) | 10/0/10 (N/R) | 100 |

[1]Observations: AN = Appeared Normal; L = lethargic; N/R = not reported

Water chemistry parameters: Temperature at time (0)=19.5° C.; Temperature at time (48 hours)=20.0° C. Dissolved oxygen ranged from 8.6-9.1 ppm in all treatment groups. At test initiation, the pH was 6.7 in the 1000 mg/L treatment group and the pH ranged from 7.9 to 8.5 in all treatment groups at 24 and 48 hours.

TABLE TT10

Formulation 2

| Conc. (mg/L) | Number Dead/Number Immobile/ Number Exposed (Observations)[1] | | Cumulative % Mortality |
|---|---|---|---|
| | 24 Hours | 48 Hours | |
| Common Control | 0/0/20 (20 AN) | 0/0/20 (20 AN) | 0 |
| 81 | 0/0/10 (10 AN) | 0/0/10 (10 AN) | 0 |
| 130 | 0/0/10 (10 AN) | 0/1/10 (8 AN; 1 L) | 10 |
| 216 | 0/0/10 (8 AN; 2 L) | 4/5/10 (1 L) | 90 |
| 360 | 0/5/10 (5 L) | 10/0/10 (N/R) | 100 |
| 600 | 5/3/10 (2 L) | 10/0/10 (N/R) | 100 |
| 1000 | 9/0/10 (1 L) | 10/0/10 (N/R) | 100 |

[1]Observations: AN = Appeared Normal; L = lethargic; N/R = not reported

Water chemistry parameters: Temperature at time (0)=19.5° C.; Temperature at time (48 hours)=20.0° C. Dissolved oxygen ranged from 8.6-9.1 ppm in all treatment groups. At test initiation, the pH was 6.7 in the 1000 mg/L treatment group and the pH ranged from 7.9 to 8.5 in all treatment groups at 24 and 48 hours.

TABLE TT11

Formulation 3

| Conc. (mg/L) | Number Dead/Number Immobile/ Number Exposed (Observations)[1] | | Cumulative % Mortality |
|---|---|---|---|
| | 24 Hours | 48 Hours | |
| Common Control | 0/0/20 (20 AN) | 0/0/20 (20 AN) | 0 |
| 130 | 0/0/10 (10 AN) | 0/0/10 (10 AN) | 0 |
| 216 | 0/0/10 (10 AN) | 0/0/10 (9 AN; 1 L) | 0 |
| 360 | 0/0/10 (10 AN) | 3/1/10 (2 AN; 4 L) | 40 |
| 600 | 0/2/10 (8 AN) | 6/0/10 (2 AN; 2 L) | 60 |
| 1000 | 3/1/10 (6 L) | 10/0/10 (N/R) | 100 |

[1]Observations: AN = Appeared Normal; L = lethargic; N/R = not reported

Water chemistry parameters: Temperature at time (0)=19.5° C.; Temperature at time (48 hours)=20.0° C. Dissolved oxygen ranged from 8.3-8.5 ppm in all treatment groups. At test initiation, the pH was 7.0 in the 1000 mg/L treatment group and the pH ranged from 7.7 to 8.6 in all treatment groups at 24 and 48 hours.

TABLE TT12

Formulation 3 (repeat)

| Conc. (mg/L) | Number Dead/Number Immobile/ Number Exposed (Observations)[1] | | Cumulative % Mortality |
|---|---|---|---|
| | 24 Hours | 48 Hours | |
| Common Control | 0/0/20 (20 AN) | 0/0/20 (20 AN) | 0 |
| 130 | 0/0/10 (10 AN) | 0/0/10 (10 AN) | 0 |
| 216 | 0/0/10 (10 AN) | 0/0/10 (10 AN) | 0 |
| 360 | 0/3/10 (7 AN) | 3/0/10 (7 AN) | 30 |
| 600 | 0/2/10 (8 AN) | 7/1/10 (2 AN) | 80 |
| 1000 | 1/3/10 (6 L) | 10/0/10 (N/R) | 100 |

[1]Observations: AN = Appeared Normal; L = lethargic; N/R = not reported

Water chemistry parameters: Temperature at time (0)=18.6° C.; Temperature at time (48 hours)=20.1° C. Dissolved oxygen ranged from 8.7-9.1 ppm in all treatment groups. At test initiation, the pH was 6.7 in the 1000 mg/L treatment group and the pH ranged from 7.6 to 8.3 in all treatment groups at 24 and 48 hours.

TABLE TT13

Formulation 4

| Conc. (mg/L) | Number Dead/Number Immobile/Number Exposed (Observations)[1] | | Cumulative % Mortality |
|---|---|---|---|
| | 24 Hours | 48 Hours | |
| Common Control | 0/0/20 (20 AN) | 0/0/20 (20 AN) | 0 |
| 216 | 0/0/10 (10 AN) | 0/0/10 (10 AN) | 0 |
| 360 | 0/0/10 (10 AN) | 0/0/10 (10 AN) | 0 |
| 600 | 1/0/10 (8 AN; 1 L) | 6/0/10 (4 AN) | 60 |
| 1000 | 0/3/10 (4AN; 3 L) | 8/0/10 (2 L) | 80 |
| 1600 | 0/5/10 (4AN; 1 L) | 8/1/10 (1 L) | 90 |

[1]Observations: AN = Appeared Normal; L = lethargic; N/R = not reported

Water chemistry parameters: Temperature at time (0)=19.5° C.; Temperature at time (48 hours)=20.0° C. Dissolved oxygen ranged from 8.3-8.7 ppm in all treatment groups. At test initiation, the pH was 6.7 in the 1600 mg/L treatment group and the pH ranged from 7.7 to 8.5 in all treatment groups at 24 and 48 hours.

Analysis of the data from Tables TT5 through TT13 indicates significantly lower toxicity for the compositions of the present invention versus the prior art and comparative compositions.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. A stable composition comprising glyphosate or a salt or ester thereof, a derivatized saccharide surfactant, and an amine oxide surfactant, wherein said amine oxide comprises a surfactant of the formula:

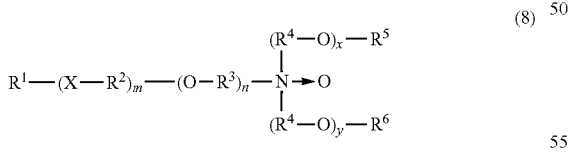

(8)

wherein $R^1$ is a $C_{1-22}$ straight or branched chain hydrocarbyl; each X is independently an ether, thioether, sulfoxide, ester, thioester or amide linkage; each $R^2$ is independently $C_{2-6}$ alkylene; each $R^3$ and $R^4$ are independently $C_{2-4}$ alkylene; and $R^5$ and $R^6$ are independently hydrogen, $C_{1-4}$ alkyl or $C_{2-4}$ acyl; x and y are average numbers such that the sum of x and y is from about 2 to about 60; m is from 0 to about 9; and n is from 0 to about 5;

provided that when m and n are 0, and $R^5$ and $R^6$ are H, $R^1$ is $C_{9-22}$ hydrocarbyl;

and wherein the weight ratio of the derivatized saccharide surfactant to the amine oxide surfactant is greater than 1:1.

2. The composition of claim 1 wherein $R^5$ and $R^6$ are hydrogen.

3. The composition of claim 1 wherein $R^3$ and $R^4$ are each independently selected from the group consisting of ethylene, n-propylene, and i-propylene.

4. The composition of claim 3 wherein $R^4$ is ethylene.

5. The composition of claim 1 wherein the sum of x and y is from about 2 to about 20.

6. The composition of claim 1 wherein m and n are 0, $R^1$ is $C_{9-22}$ straight or branched chain alkyl, and $R^5$ and $R^6$ are hydrogen.

7. The composition of claim 6 wherein $R^4$ is ethylene and the sum of x and y is from about 2 to about 20.

8. A stable composition comprising glyphosate or a salt or ester thereof, a derivatized saccharide surfactant, and an amine oxide surfactant of the formula:

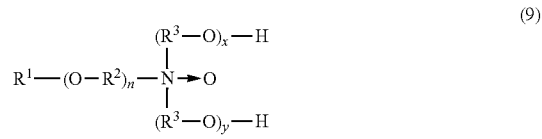

(9)

wherein $R^1$ is straight or branched chain $C_{6-22}$ alkyl, aryl, or alkylaryl group; n is an average number from 0 to about 10; $R^2$ in each of the $(O-R^2)_n$ groups is independently $C_{1-4}$ alkylene; each of the $R^3$ groups is independently $C_{1-4}$ alkylene; and x and y are average numbers such that the sum of x and y is from 2 to about 20;

provided that when n is 0, $R^1$ is straight or branched chain $C_{9-22}$ alkyl;

and wherein the weight ratio of the derivatized saccharide surfactant to the amine oxide surfactant is greater than 1:1.

9. The composition of claim 8 wherein $R^1$ is a straight or branched chain alkyl group having from about 8 to about 18 carbon atoms; $R^3$ is independently selected from the group consisting of i-propylene and ethylene; and the sum of x and y is from 2 to 10.

10. A stable composition comprising glyphosate or a salt or ester thereof, a derivatized saccharide surfactant, and an amine oxide surfactant of the formula:

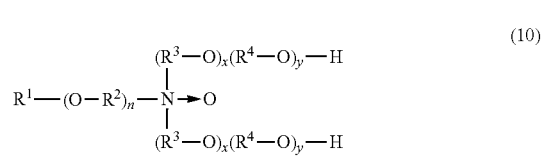

(10)

wherein $R^1$ is straight or branched chain $C_{6-22}$ alkyl, aryl, or alkylaryl group; n is an average number from 0 to about 10; each of the $R^2$, $R^3$ and $R^4$ groups are independently $C_{1-4}$ alkylene; and x and y are average numbers such that the sum of x and y is from 2 to about 20;

provided that when n is 0, $R^1$ is straight or branched chain $C_{9-22}$ alkyl;

and wherein the weight ratio of the derivatized saccharide surfactant to the amine oxide surfactant is greater than 1:1.

11. The composition of claim 10 wherein the composition comprises a salt of glyphosate selected from the isopropylamine, trimethylsulfonium, monoethanolammonium, monoammonium, diammonium, sodium, and potassium salts thereof.

12. The composition of claim 11 wherein the composition comprises glyphosate in the form of the potassium salt thereof.

13. The composition of claim 11 wherein the composition comprises glyphosate in the form of the isopropylamine salt thereof.

14. The composition of claim 10 wherein the composition is an aqueous concentrate wherein the glyphosate concentration is from about 400 to about 600 grams acid equivalent per liter.

15. The composition of claim 10 wherein the composition is an aqueous application mixture wherein the glyphosate concentration is from about 1 to about 20 grams acid equivalent per liter.

16. The composition of claim 11 wherein the composition comprises glyphosate in the form of the ammonium, diammonium or sodium salt thereof, and the composition is a solid concentrate wherein the glyphosate concentration is from about 20 to about 90 percent by weight of the total composition on an acid equivalent basis.

17. The composition of claim 10 wherein the weight ratio of glyphosate acid equivalent to total surfactant is from about 2:1 to about 10:1.

18. The composition of claim 17 wherein the weight ratio of glyphosate acid equivalent to total surfactant is from about 2:1 to about 5:1.

19. The composition of claim 10 wherein said derivatized saccharide comprises a surfactant of the formula:

$$R^{11}\text{—O-(sug)}_u \quad (2),$$

$$(\text{sug})_u\text{-(OC(O)R}^{21})_x \quad (3A),$$

$$(\text{sug})_u(\text{C(O)—OR}^{21})_x \quad (3B),$$

$$R^{41}\text{—(NR}^{42})_n\text{-(sug)}_u \quad (6), \text{ or}$$

$$R^{51}\text{-(sug)}_u(\text{O-organosiloxane})_z \quad (7),$$

wherein:
$R^{11}$ is a straight or branched chain $C_{4-22}$ hydrocarbyl;
$R^{21}$ is a straight or branched chain alkyl or alkenyl group having from about 4 to about 22 carbon atoms;
$R^{41}$ is a straight or branched chain substituted or unsubstituted hydrocarbyl selected from alkyl, alkenyl, alkylphenyl, and alkenylphenyl having from about 4 to about 22 carbon atoms;
$R^{42}$ is hydrogen or $C_{1-4}$ hydrocarbyl;
n is an average number of from 0 to about 1;
$R^{51}$ is a straight or branched chain alkyl or alkenyl group having from about 8 to about 22 carbon atoms;
z is an average number of from about 2 to about 5;
sug is an open or cyclic saccharide residue selected from the group consisting of ribose, xylose, arabinose, glucose, galactose, mannose, telose, gulose, allose, altrose, idose, lyxose, ribulose, sorbose (sorbitan) and fructose;
sug is a disaccharide selected from maltose, lactose and sucrose, or
sug is a disaccharide, oligosaccharide or polysaccharide selected from two or more identical saccharides or two or more different saccharides selected from the group consisting of ribose, xylose, arabinose, glucose, galactose, mannose, telose, gulose, allose, altrose, idose, lyxose, ribulose, sorbose (sorbitan) and fructose;

x is an average number of from about 1 to about 5; and
u is an average number of from 1 to about 10;
or wherein said derivatized saccharide comprises a surfactant of the formula:

$$(\text{sug})_u[\text{-(OR}^{31})_x R^{32}]_y[\text{—(OR}^{31})_x \text{OH})(\text{—(OR}^{31})_x R^{33})]_z \quad (4)$$

wherein each $R^{31}$ is independently an alkyl having from 2 to about 4 carbon atoms; each $R^{32}$ is independently selected from —OH and —OC(O)$R^{34}$; and $R^{33}$ is —OC(O)$R^{34}$, wherein each $R^{34}$ is independently selected from an straight or branched chain alkyl or alkenyl group having from about 4 to about 22 carbon atoms;
each x is independently an average number of from about 0 to about 20, and the sum of each x is from 1 to about 60;
y is an average number of from about 0 to about 5 times u;
and sug and u are as defined above.

20. The composition of claim 19 wherein said derivatized saccharide comprises a surfactant of formula (2):

$$R^{11}\text{—O-(sug)}_u \quad (2)$$

wherein $R^{11}$ is a straight or branched chain $C_{4-22}$ hydrocarbyl;
sug is an open or cyclic saccharide residue selected from the group consisting of ribose, xylose, arabinose, glucose, galactose, mannose, telose, gulose, allose, altrose, idose, lyxose, ribulose, sorbose (sorbitan) and fructose,
sug is a disaccharide selected from maltose, lactose and sucrose, or
sug is a disaccharide, oligosaccharide or polysaccharide selected from two or more identical saccharides or two or more different saccharides selected from the group consisting of ribose, xylose, arabinose, glucose, galactose, mannose, telose, gulose, allose, altrose, idose, lyxose, ribulose, sorbose (sorbitan) and fructose; and
u is an average number of from 1 to about 10.

21. The composition of claim 20 wherein $R^{11}$ is straight or branched chain $C_{8-18}$ alkyl, sug is glucose and u is an average number from 1 to about 5.

22. The composition of claim 19 wherein said derivatized saccharide comprises a surfactant of formula (3A) or (3B):

$$(\text{sug})_u\text{-(OC(O)R}^{21})_x \quad (3A)$$

$$(\text{sug})_u(\text{C(O)—OR}^{21})_x \quad (3B)$$

wherein $R^{21}$ is a straight or branched chain alkyl or alkenyl group having from about 4 to about 22 carbon atoms;
u is from 1 to about 10;
x is an average number of from about 1 to about 5; and
sug is an open or cyclic saccharide residue selected from the group consisting of ribose, xylose, arabinose, glucose, galactose, mannose, telose, gulose, allose, altrose, idose, lyxose, ribulose, sorbose (sorbitan) and fructose,
sug is a disaccharide selected from maltose, lactose and sucrose, or
sug is a disaccharide, oligosaccharide or polysaccharide selected from two or more identical saccharides or two or more different saccharides selected from the group consisting of ribose, xylose, arabinose, glucose, galactose, mannose, telose, gulose, allose, altrose, idose, lyxose, ribulose, sorbose (sorbitan) and fructose.

23. The composition of claim 10 wherein said derivatized saccharide comprises a surfactant of formula (4):

$$(\text{sug})_u[\text{-(OR}^{31})_x R^{32}]_y[\text{—(OR}^{31})_x \text{OH})(\text{—(OR}^{31})_x R^{33})]_z \quad (4)$$

wherein each $R^{31}$ is independently an alkyl having from 2 to about 4 carbon atoms; each $R^{32}$ is independently selected from —OH and —OC(O)$R^{34}$; and $R^{33}$ is —OC(O)$R^{34}$, wherein each $R^{34}$ is independently selected from an straight or branched chain alkyl or alkenyl group having from about 4 to about 22 carbon atoms;

each x is independently an average number of from about 0 to about 20, and the sum of each x is from 1 to about 60;

y is an average number of from about 0 to about 5 times u;

sug is an open or cyclic saccharide residue selected from the group consisting of ribose, xylose, arabinose, glucose, galactose, mannose, telose, gulose, allose, altrose, idose, lyxose, ribulose, sorbose (sorbitan) and fructose, sug is a disaccharide selected from maltose, lactose and sucrose, or sug is a disaccharide, oligosaccharide or polysaccharide selected from two or more identical saccharides or two or more different saccharides selected from the group consisting of ribose, xylose, arabinose, glucose, galactose, mannose, telose, gulose, allose, altrose, idose, lyxose, ribulose, sorbose (sorbitan) and fructose; and u is an average number of from about 1 to about 10.

24. The composition of claim 10 wherein the weight ratio of the derivatized saccharide surfactant to the amine oxide surfactant is from about 2:1 to about 10:1.

25. The composition of claim 24 wherein the weight ratio of the derivatized saccharide surfactant to the amine oxide surfactant is from about 2:1 to about 8:1.

26. The composition of claim 25 wherein the weight ratio of the derivatized saccharide surfactant to the amine oxide surfactant is from about 2:1 to about 6:1.

27. The composition of claim 10 wherein cloud point is at least 50° C.

28. The composition of claim 10 wherein the composition does not exhibit phase separation upon exposure to temperatures up to about 50° C. for 14 days.

29. The composition of claim 10 wherein the composition does not form crystals of glyphosate or salt thereof upon exposure to a temperature of about 0° C. for a period of up to about 7 days.

30. The composition of claim 29 wherein the composition does not form crystals of glyphosate or salt thereof upon exposure to a temperature of about −10° C. for a period of up to about 7 days.

31. The composition of claim 10 wherein the concentrations of said derivatized saccharide and said amine oxide surfactants are such that the composition exhibits lesser aquatic toxicity on an $EC_{50}$ basis than a reference composition as measured by at least one of EPA method 2002.0, EPA method 1002, EPA method 2000.0, EPA method 1000, EPA method 2019.0, OECD Guideline 202 or the method of Annex V of European Union Directive 67/548/EEC, but provides plant growth control of at least 85 percent of the growth control provided by the reference composition when the composition and reference composition are applied to the plants at the same glyphosate acid equivalent application rate, said reference composition being devoid of said derivatized saccharide but otherwise identical to said low toxicity composition in the nature and concentration of its herbicide, amine oxide surfactant and any other herbicidally active components.

32. The composition of claim 10 wherein the concentrations of said derivatized saccharide and said amine oxide surfactants are such that the composition exhibits greater biodegradability than a reference composition as measured by at least one of ASTM method D-5864, CEC method L-33-A-934, OECD method 301, OECD method 302B, or EPA method 560/6-82-003, but provides growth control of at least 85 percent of the growth control provided by the reference composition when the composition and reference composition are applied to the plants at the same glyphosate acid equivalent application rate, said reference composition being devoid of said derivatized saccharide but otherwise identical to said low toxicity composition in the nature and concentration of its herbicide, amine oxide surfactant and any other herbicidally active components.

33. The composition as set forth in claim 31 wherein the $EC_{50}$ concentration is at least 360 milligrams per liter when measured at 48 hours according to the method of OECD Guideline 202.

34. The composition as set forth in claim 32 wherein the composition is inherently biodegradable when measured according to the method of OECD Guideline 301 or the method of OECD guideline 302B.

35. A method of controlling plant growth comprising applying the composition of claim 10 to a plant.

36. The composition of claim 10 wherein $R^1$ is a straight or branched chain alkyl group having from about 8 to about 18 carbon atoms; $R^3$ and $R^4$ are independently selected from the group consisting of i-propylene and ethylene; and the sum of x and y is from 2 to 10.

37. The composition of claim 10 wherein $R^1$ is $C_{12}$ alkyl; n is 0; $R^3$ is ethylene; $R^4$ is n-propylene; x is 9; and y is 2.

* * * * *